(12) United States Patent
Rios et al.

(10) Patent No.: US 7,906,486 B2
(45) Date of Patent: Mar. 15, 2011

(54) METHOD OF TREATING OR PREVENTING TISSUE DETERIORATION, INJURY OR DAMAGE DUE TO DISEASE OF MUCOSA

(75) Inventors: Israel Rios, Menlo Park, CA (US); Cynthia Tuthill, Menlo Park, CA (US)

(73) Assignee: SciClone Pharmaceuticals, Inc., Foster City, CA (US)

( * ) Notice: Subject to any disclaimer, the term of this patent is extended or adjusted under 35 U.S.C. 154(b) by 0 days.

(21) Appl. No.: 12/526,585

(22) PCT Filed: Feb. 11, 2008

(86) PCT No.: PCT/US2008/001768
§ 371 (c)(1),
(2), (4) Date: Aug. 10, 2009

(87) PCT Pub. No.: WO2008/100458
PCT Pub. Date: Aug. 21, 2008

(65) Prior Publication Data
US 2010/0086622 A1   Apr. 8, 2010

Related U.S. Application Data

(60) Provisional application No. 60/900,977, filed on Feb. 13, 2007.

(51) Int. Cl.
*A61K 38/02* (2006.01)
(52) U.S. Cl. ........................................................ 514/19
(58) Field of Classification Search ...................... 514/19
See application file for complete search history.

(56) References Cited

U.S. PATENT DOCUMENTS

| | | | |
|---|---|---|---|
| 4,125,626 A | 11/1978 | Orlowski et al. | |
| 4,568,489 A | 2/1986 | Floyd | |
| 4,758,551 A | 7/1988 | Meister et al. | |
| 4,766,106 A | 8/1988 | Katre et al. | |
| 4,895,835 A | 1/1990 | Hasegawa | |
| 4,968,672 A | 11/1990 | Jacobson et al. | |
| 5,206,220 A | 4/1993 | Hilton | |
| 5,736,519 A | 4/1998 | Deigin et al. | |
| 5,744,452 A | 4/1998 | Kolobov et al. | |
| 5,877,147 A | 3/1999 | Pinegin | |
| 5,888,980 A | 3/1999 | Ripka | |
| 5,916,878 A | 6/1999 | Kolobov et al. | |
| 6,060,452 A | 5/2000 | Green et al. | |
| 7,173,013 B2 | 2/2007 | Kolobov et al. | |
| 2002/0177226 A1 | 11/2002 | Kozhemyakin et al. | |
| 2005/0256042 A1 | 11/2005 | Jeffers et al. | |
| 2006/0094665 A1 | 5/2006 | Green | |
| 2007/0087974 A1 | 4/2007 | Tuthill et al. | |
| 2009/0074815 A1 | 3/2009 | Tuthill et al. | |
| 2009/0088392 A1 | 4/2009 | Tuthill et al. | |
| 2009/0143313 A1 | 6/2009 | Mossel et al. | |
| 2010/0204295 A1 | 8/2010 | Kolobov et al. | |

FOREIGN PATENT DOCUMENTS

| | | |
|---|---|---|
| EP | 1020179 | 7/2000 |
| RU | 2120298 | 10/1998 |
| WO | WO 92/17191 | 10/1992 |
| WO | WO 93/08815 | 5/1993 |
| WO | WO 94/20063 | 9/1994 |
| WO | WO 96/40740 | 12/1996 |
| WO | WO 97/19691 | 6/1997 |
| WO | WO 03/013572 | 2/2003 |
| WO | 2005112639 A2 | 12/2005 |
| WO | WO 2006/047702 | 5/2006 |
| WO | WO 2006/076169 | 7/2006 |
| WO | WO 2006/116053 | 11/2006 |
| WO | WO 2008/076443 | 6/2008 |
| WO | WO 2008/143824 | 11/2008 |
| WO | WO 2009/025830 | 2/2009 |
| WO | WO 2010/017178 | 2/2010 |

OTHER PUBLICATIONS

Kian Ang et al. J. Clin. Oncol., 2005, vol. 23, No. 13, pp. 3008-3015.*
Cerchietti, Leandro C.A., et al., "Double-Blinded, Placebo-Controlled Trial on Intravenous I-alanyl-I-glutamine in the Incidence of Oral Mucositis following chemoradiotherapy in patients with head-and-neck cancer", International Journal of Radiation Oncology Biology Physics, vol. 65, No. 5; 2006; p. 1330-1337.
Epstein, J. B., et al., "Emerging Approaches for Prophylaxis and Management of Oropharyngeal Mucositis in Cancer Therapy", Expert Opinion on Emerging Drugs, vol. 11, No. 2, May 2006, p. 353-373.
Savarese, D., et al., "Prevention of Chemotherapy and radiation toxicity with glutamine", Cancer Treatment Reviews, vol. 29, Jun. 24, 2003, p. 501-513.
EP08725404 Supplementary European Search Report mailed Mar. 9, 2010.
PCT/US2008/01768 International Search Report mailed Aug. 1, 2008.
PCT/US2008/01768 IPRP and Written Opinion mailed Aug. 27, 2009.
U.S. Appl. No. 12/600,584, Kolobov et al.
U.S. Appl. No. 12/674,646, Tuthill.
International Search Report and Written Opinion for PCT/US08/01768, mailed Aug. 1, 2008.
International Preliminary Report on Patentability for PCT/US08/01768, issued on Aug. 19, 2009.
Database IMSDRUGNEWS, R & D Focus Drug News, XP-002377619, Sep. 6, 1999.
Database CIN, Other Research News, XP-002377620, Feb. 28, 2000.
Database IMSDRUGNEWS, R & D Focus Drug News, XP-002377621, Jan. 22, 2001.
Hasegawa et al., "γ-Glutamylpeptide Formative Activity of Corynebacterium glutamicum by the Reverse Reaction of the γ-Glutamylpeptide Hydrolytic Enzyme," Agric. Biol. Chem., vol. 42, No. 2, pp. 371-381, (1978).
Hirata et al., "Studies on Separation of Amino Acids and Related Compounds, VIII. Separation of L-Aspartyl-(α,β)-L-histidine and of L-Glutamyl-(α,γ)-L-Histidine," Bulletin of the Chemical Society of Japan, vol. 45, No. 6, 1972, pp. 1790-1794.
Kian Ang, K. et al., "Concomitant Boost Radiation Plus Concurrent Cisplatin for Advanced Head and Neck Carcinomas: Radiation Therapy Oncology Group Phase II Trial 99-14," Journal of Clinical Oncology, May 1, 2005, vol. 23, No. 13, pp. 3008-3015.

(Continued)

Primary Examiner — James D Anderson
(74) Attorney, Agent, or Firm — Cooley LLP

(57) ABSTRACT

An immunomodulatory compound is utilized to treat mucosa disease.

13 Claims, No Drawings

OTHER PUBLICATIONS

Li, K. W. et al., "The antinatriuretic Action of γ-L-glutamyl-5-hydroxy-L-tryptophan is dependent on its decarboxylation to 5-hydroxytryptamine in normal man," Br. J. Clin. Pharmac., 387, pp. 265-269 (1994).

Prezioso et al., "γ-Glutamyltranspeptidase Expression Regulates the Growth-Inhibitory Activity of Anti-Tumor Prodrug γ-L-gultaminyl-4-hydroxy-3-iodobenzene," Int. J. Cancer, 56, pp. 874-879 (1994).

Smith, D. L. et al., "Natural Killer Cell Cytolytic Activity is Necessary for In Vivo Antitumor Activity of the Dipeptide L-Glutamyl-L-Tryptophan," Int. J. Cancer, 2003, vol. 106, pp. 528-533.

Wellner, D., "Separation of γ-Glutamyl Amino Acids by Ion-Exchange Chromatography," Methods in Enzymology, vol. 113, 1985, pp. 564-566.

\* cited by examiner

METHOD OF TREATING OR PREVENTING TISSUE DETERIORATION, INJURY OR DAMAGE DUE TO DISEASE OF MUCOSA

CROSS REFERENCE TO RELATED APPLICATION

This application is a 35 U.S.C. §371 National Phase Entry Application from PCT/US2008/001768, filed Feb. 11, 2008, and designating the United States. This application also claims the benefit of U.S. Provisional Application No. 60/900,977, filed Feb. 13, 2007, the disclosure of which is incorporated herein in its entirety by reference.

BACKGROUND OF THE INVENTION

1. Field of the Invention

The present invention relates to the field of mucosa disease treatment.

2. Description of the Background Art

Oral ulcerative mucositis is a common, painful, dose-limiting toxicity of drug and radiation therapy for cancer. The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of patients receiving anti-neoplastic drug therapy. The frequency and severity are significantly greater among patients who are treated with induction therapy for leukemia or with many of the conditioning regimens for bone marrow transplant. Among these individuals, moderate to severe mucositis is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through three stages:
1. Inflammation accompanied by painful mucosal erythema, which can respond to local anesthetics.
2. Painful ulceration with pseudomembrane formation and, in the case of myelosuppressive treatment, potentially life-threatening sepsis, requiring antimicrobial therapy. Pain is often of such intensity as to require parenteral narcotic analgesia.
3. Spontaneous healing, occurring about 2-3 weeks after cessation of anti-neoplastic therapy.

Standard therapy for mucositis is predominantly palliative, including application of topical analgesics such as lidocaine and/or systemic administration of narcotics and antibiotics. Currently, there is only one approved treatment for oral mucositis, Kepivance (Palifermin), which is only approved for the treatment of oral mucositis in patients undergoing conditioning regimens prior to hematopoetic stem cell transplantation for the treatment of hematologic malignancies.

The complexity of mucositis as a biological process has only been recently appreciated. It has been suggested that the condition represents a sequential interaction of oral mucosal cells and tissues, reactive oxygen species, pro-inflammatory cytokines, mediators of apoptosis and local factors such as saliva and the oral micro biota. While epithelial degeneration and breakdown ultimately result in mucosal ulceration, it appears that the early changes associated with radiation-induced mucosal toxicity occur within the endothelium, and connective tissue of the submucosa. Electron microscopic evaluation of mucosa within 1 week of radiation shows damage to both endothelium and connective tissue, but not epithelium. Such injury is likely mediated by free radical formation. It appears that the overall mechanism for mucositis development is similar for both radiation and chemotherapy.

There remains a need in the art for improvements in methods for treating or preventing mucosa diseases.

SUMMARY OF THE INVENTION

In accordance with one aspect, a method of treatment for treating, preventing, inhibiting or reducing tissue deterioration, injury or damage due to disease of mucosa, or for restoring tissue adversely affected by said disease, in a subject, comprises administering to said target subject an effective amount of an immunomodulator compound of formula A:

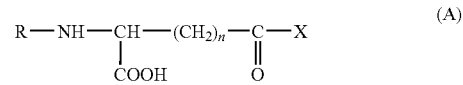

In Formula A, n is 1 or 2, R is hydrogen, acyl, alkyl or a peptide fragment, and X is an aromatic or heterocyclic amino acid or a derivative thereof, wherein said immunomodulator compound is administered to said target subject without administering said at least one interferon to said target subject. Preferably, X is L-tryptophan or D-tryptophan. The invention also relates to use of a compound of formula A in preparation of a medicament for treatment of mucosa disease.

DESCRIPTION OF THE PREFERRED EMBODIMENTS

The present invention is applicable to mucosa diseases or disease manifestations thereof. In preferred embodiments, the mucosa disease results from radiation and/or chemotherapy of a subject, preferably in a human patient. The radiation may be acute or fractionated. The mucosa disease may result from a combination of radiation and chemotherapy. In certain embodiments, the disease is of oral and/or esophageal mucosa, e.g., mocositis and/or ulcerative lesions.

In accordance with one embodiment, the present invention relates to treatment of mucositis by administering an immunomodulator compound to a mammalian subject, preferably a human patient.

In certain embodiments, the immunomodulatory compounds of the present invention are administered before, during and/or after administration of radiation and/or a chemotherapeutic agent to a patient. Radiation often is administered in multiple doses, and mucosa disease occurs in virtually all patients who receive radiation therapy for tumors of the head and neck, typically beginning with cumulative exposures of 15 Gy radiation and then worsening at total cumulative doses of 60 Gy radiation or more. In preferred embodiments, an immunomodulator compound according to the invention is administered before, during or after administration of 7-8 Gy (e.g., 7.5 Gy) radiation to a patient, 15 Gy, 40 Gy, 60 Gy, or more radiation to patient.

The immunomodulator compounds of the invention also can be administered for the treatment or prevention of mucosa disease resulting from administration of chemotherapy agents, such as cis-platin, e.g., administered at a dosage within a range of about 0.1-50 mg/kg, e.g., about 5 mg/kg.

Immunomodulator compounds used in accordance with the present invention, comprise immunomodulators of Formula A:

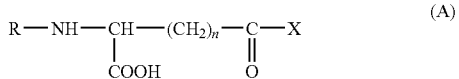

In Formula A, n is 1 or 2, R is hydrogen, acyl, alkyl or a peptide fragment, and X is an aromatic or heterocyclic amino acid or a derivative thereof. Preferably, X is L-tryptophan or D-tryptophan. Appropriate derivatives of the aromatic or heterocyclic amino acids for "X" are: amides, mono- or di-($C_1$-$C_6$) alkyl substituted amides, arylamides, and ($C_1$-$C_6$) alkyl or aryl esters. Appropriate acyl or alkyl moieties for "R" are: branched or unbranched alkyl groups of 1 to about 6 carbons, acyl groups from 2 to about 10 carbon atoms, and blocking groups such as carbobenzyloxy and t-butyloxycarbonyl. Preferably the carbon of the CH group shown in Formula A has a stereoconfiguration, when n is 2, that is different from the stereoconfiguration of X.

Preferred embodiments utilize compounds such as γ-D-glutamyl-L-tryptophan, γ-L-glutamyl-L-tryptophan, γ-L-glutamyl-$N_{in}$-formyl-L-tryptophan, N-methyl-γ-L-glutamyl-L-tryptophan, N-acetyl-γ-L-glutamyl-L-tryptophan, γ-L-glutamyl-D-tryptophan, β-L-aspartyl-L-tryptophan, and β-D-aspartyl-L-tryptophan. Particularly preferred embodiments utilize γ-D-glutamyl-L-tryptophan, sometimes referred to as SCV-07. These compounds, methods for preparing these compounds, pharmaceutically acceptable salts of these compounds and pharmaceutical formulations thereof are disclosed in U.S. Pat. No. 5,916,878, incorporated herein by reference.

SCV-07, γ-D-glutamyl-L-tryptophan, is a member of a class of immunomodulatory drugs that possess γ-glutamyl or β-aspartyl moieties, which was discovered by Russian scientists and is being examined for efficacy in several indications in the U.S. by SciClone Pharmaceuticals, Inc. SCV-07 possesses a number of immunomodulatory activities in vivo and in vitro. SCV-07 increases Con-A-induced thymocyte and lymphocyte proliferation, increases Con-A-induced interleukin-2 (IL-2) production and IL-2 receptor expression by spleen lymphocytes, and stimulates expression of Thy-1.2 on bone marrow cells. In vivo, SCV-07 has a strong immunostimulatory effect on 5-FU-immune-suppressed animals and in a model of immunization with sheep red blood cells.

The Formula A compounds may be administered as dosages in the range of about 0.001-2000 mg, more preferably about 0.01-100 mg. Dosages may be administered one or more times per week, preferably on a daily basis, with dosages administered one or more times per day. Administration can be by any suitable method, including orally, nasally, transdermally, sublingually, by injection, periodic infusion, continuous infusion, and the like. The dosages may be administered by intramuscular injection, although other forms of injection and infusion may be utilized, and other forms of administration such as oral or nasal inhalation or oral ingestion may be employed.

Dosages may also be measured in micrograms per kilogram, with dosages in the range of about 0.1-10,000 ug/kg, more preferably within the range of about 1.0-1000 ug/kg.

Included are biologically active analogs having substituted, deleted, elongated, replaced, or otherwise modified portions which possess bioactivity substantially similar to that of SCV-07, e.g., an SCV-07 derived peptide having sufficient homology with SVC-07 such that it functions in substantially the same way with substantially the same activity as SCV-07.

In some embodiments, the Formula A compound is present in a pharmaceutically acceptable liquid carrier, such as water for injection, saline in physiological concentrations, or similar, or in tablet form with suitable dry carrier(s) and excipient(s).

Effective amounts of Formula A compound can be determined by routine dose-titration experiments.

Example 1

A First Study of SCV-07 in the Treatment of Oral Mucositis Induced by Acute Radiation in Hamsters 1. Objective The objective of this study was to conduct a preliminary evaluation of the efficacy of SCV-07 in the treatment of oral mucositis using an acute radiation induced hamster model of the disease. SCV-07 was given at doses of 1, 10 or 100 ug/kg once daily by sub-cutaneous injection for 18 days, starting one day before radiation and continuing until day 16 after radiation. No deaths were observed in any of the treatment groups and there were no statistically significant changes in growth rate, suggesting that SCV-07 was well tolerated at these doses. Animals treated with SCV-07 at 10 ug/kg on days −1 to 16 showed a statistically significant reduction in mucositis scores on day 22 (P=0.024). Animals treated with SCV-07 at 100 ug/kg on days −1 to 16 showed a statistically significant reduction in mucositis scores on day 14 (P=0.025), in addition to a statistically significant reduction in the number of animal days with a score of 3 or higher (P=0.029). These data suggest that SCV-07 demonstrated a dose dependant benefit on the severity and course of radiation induced mucositis.

Acute Radiation Model

The acute radiation model in hamsters has proven to be an accurate, efficient and cost-effective technique to provide a preliminary evaluation of anti-mucositis compounds. The course of mucositis in this model is well defined and results in peak scores approximately 14-16 Days following radiation. The acute model has little systemic toxicity, resulting in few hamster deaths, thus permitting the use of smaller groups (N=7-8) for initial efficacy studies. It has also been used to study specific mechanistic elements in the pathogenesis of mucositis. Molecules that show efficacy in the acute radiation model may be further evaluated in the more complex models of fractionated radiation, chemotherapy, or concomitant therapy.

In this study, an acute radiation dose of 40 Gy on day 0 was administered. Clinically significant mucositis was observed on days 12 through 28.

2. Study Objective and Summary

Study Objective

The objective of this study was to evaluate the effect of SCV-07, administered by sub-cutaneous injection on different schedules between the day before radiation and the sixteenth day after radiation, on the frequency, severity and duration of oral mucositis induced by acute radiation.

Study Summary

Thirty-two (32) Syrian Golden Hamsters were given an acute radiation dose of 40 Gy directed to their left buccal cheek pouch on day 0. Test materials were given by sub-cutaneous injection once daily. Dosing began one day before radiation (day −1) and continued until day 16. Mucositis was evaluated clinically starting on day 6, and continuing on alternate days until day 28.

3. Evaluation

Mucositis Evaluation

The grade of mucositis was scored, beginning day 6, and for every second day thereafter, through and including day 28. The effect on mucositis of each drug treatment compared to placebo was assessed according to the following parameters:

The difference in the number of days hamsters in each group have ulcerative (score ≧3) mucositis.

On each evaluation day, the number of animals with a blinded mucositis score of 3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores 3) when compared to the control group.

Rank Sum Differences in Daily Mucositis Scores

For each evaluation day the scores of the control group were compared to those of the treated groups using non-parametric rank sum analysis. Treatment success was considered as a statistically significant lowering of scores in the treated group on 2 or more days from day 6 to day 28.

Weights and Survival

All animals were weighed daily and their survival recorded, in order to assess possible differences in animal weight among treatment groups as an indication for mucositis severity and/or possible toxicity resulting from the treatments.

4. Study Design

Thirty-two Syrian Golden Hamsters were divided into four (4) groups of eight (8) animals each. All animals received a single dose of acute radiation of 40 Gy directed to their left buccal cheek pouch on day 0. This was accomplished by anesthetizing the animals and everting the left buccal pouch, while protecting the rest of the animals with a lead shield. Test materials were given by sub-cutaneous injection once daily as detailed in Table 1. Mucositis was evaluated clinically starting on Day 6, and continuing on alternate days until day 28.

TABLE 1

Study Design

| Group Number | Number of Animals | Treatment | Treatment Schedule* | Volume (mL) |
|---|---|---|---|---|
| 1 | 8 males | Vehicle (PBS), sc, qd | Day −1 to 16 | 0.1 mL/100 g |
| 2 | 8 males | SCV-07, sc, qd 1 µg/kg, | Day −1 to 16 | 0.1 mL/100 g |
| 3 | 8 males | SCV-07, sc, qd 10 µg/kg | Day −1 to 16 | 0.1 mL/100 g |
| 4 | 8 males | SCV-07, sc, qd 100 µg/kg | Day −1 to 16 | 0.1 mL/100 g |

*The dose on day 0 will be performed 30 minutes prior to radiation

5. Material and Methods

Location of Study Performance

The study was performed at Biomodels AAALAC accredited facility in Cambridge Mass. Approval for this study was obtained from Biomodels IACUC.

Animals

Male LVG Syrian Golden Hamsters (Charles River Laboratories), aged 5 to 6 weeks, with average body weight of 85.3 g at study commencement, were used. Animals were individually numbered using an ear punch and housed in small groups of 8 animals per cage. Animals were acclimatized prior to study commencement. During this period of 5 days, the animals were observed daily in order to reject animals that present in poor condition.

Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained.

Diet

Animals were fed with a Purina Labdiet® 5061 rodent diet and water was provided ad libitum.

Animal Randomization and Allocations

Animals were randomly and prospectively divided into four (4) treatment groups prior to irradiation. Each animal was identified by an ear punch corresponding to an individual number. For more consistent identification, ear punch numbering was used rather than tagging, since tags may become dislodged during the course of the study. A cage card was used to identify each cage or label marked with the study number (SCI-01), treatment group number and animal numbers.

Sub-Cutaneous Dosing and Drug Application

The test compound, SCV-07 was provided as a powder and dissolved in sterile PBS immediately prior to administration. Three dilutions were prepared: 100 µg/mL, 10 µg/mL and 1 µg/mL. Drug was given in a volume of 0.1 mL per 100 g body weight, with the appropriate dilution of SCV-07 for each group, using a tuberculin syringe with a 27G needle. Injections were given subcutaneously to the back or abdomen.

Mucositis Induction

Mucositis was induced using a standardized acute radiation protocol. A single dose of radiation (40 Gy/dose) was administered to all animals on day 0. Radiation was generated with a 160 kilovolt potential (15-ma) source at a focal distance of 30 cm, hardened with a 0.35 mm Cu filtration system. Irradiation targeted the left buccal pouch mucosa at a rate of 3.2 Gy/minute. Prior to irradiation, animals were anesthetized with an intraperitoneal injection of Ketamine (160 mg/kg) and Xylazine (8 mg/kg). The left buccal pouch was everted, fixed and isolated using a lead shield to protect all other parts of the hamster's body.

Mucositis Scoring

The mucositis score, weight change and survival were measured throughout the study as described above. For the evaluation of mucositis, the animals were anesthetized with an inhalation anesthetic, and the left pouch everted. Mucositis was scored visually by comparison to a validated photographic scale, ranging from 0 for normal, to 5 for severe ulceration (clinical scoring). In descriptive terms, this scale is defined as follows:

TABLE 2

Mucositis Scoring.

| Score: | Description: |
| --- | --- |
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

6. Results and Discussion 6.1 Survival

No deaths were observed during the course of this study.

6.2 Weight Change

The mean daily percent weight change data was evaluated. The saline (PBS) treated control hamsters gained an average of 70.4% of their starting weight during the study. Hamsters in the group receiving SCV-07 at 1 ug/kg on days −1 to 16 gained an average of 68.4% of their starting weight during the study. Hamsters in the group receiving SCV-07 at 10 ug/kg on days −1 to 16 gained an average of 70.3% of their starting weight during the study. Hamsters in the group receiving SCV-07 at 100 ug/kg on days −1 to 16 gained an average of 82.0% of their starting weight during the study. The significance of these differences was evaluated by calculating the area-under-the-curve (AUC) for the weight gain of each animal, and then comparing the different treatment groups using a One-Way ANOVA test. The results of this analysis indicated that there were no significant differences between the different treatment groups (P=0.191).

6.3 Mucositis (Tables 3 & 4)

Mean daily mucositis scores for each group were calculated. In the saline treated control group, peak levels of mucositis were seen on day 20, when the mean score reached 3.8. The group receiving SCV-07 at 1 ug/kg from day −1 to 16 had a peak mean mucositis score of 3.8 on day 16. The group receiving SCV-07 at 10 ug/kg from day −1 to 16 had a peak mean mucositis score of 3.7 on day 16. The group receiving SCV-07 at 100 ug/kg from day −1 to 16 had a peak mean mucositis score of 3.4 on day 18. The significance of the differences observed between the different treatment groups was evaluated by calculating the number of days with a score of 3 or higher for each group and comparing these numbers using a chi-squared test. The results of this analysis are shown in Table 2. The hamsters in the saline treated control group had a score of 3 or higher on 46.9% of the animal days evaluated. In the group receiving SCV-07 at 1 ug/kg from day −1 to 16, a mucositis score of 3 or higher also was observed on 46.9% of the animals days evaluated. The hamsters in the groups treated with SCV-07 at 10 ug/kg on days −1 to 16 had a score of 3 or higher on 37.5% of animal days respectively, which was not statistically significantly different from the controls (P=0.079). The group treated with SCV-07 at 100 ug/kg on days −1 to 16 on days 1 to 16 had a score of 3 or higher on 35.4% of animal days, which was significantly different from controls (P=0.029).

A further analysis of the mucositis scores was performed using the Mann-Whitney rank sum analysis to compare the scores for each group on each day. The results of this analysis are shown in Table 4. In this analysis, 2 days of significant reduction in the mucositis score are generally required before it is regarded as meaningful reduction in mucositis. The group treated with SCV-07 at 1 ug/kg on days −1 to 16 did not show any statistically significant improvement on any day of the study, relative to the saline controls. The group treated with SCV-07 at 10 ug/kg on days −1 to 16 showed significant improvement relative to controls on day 22 (P=0.024). The group treated with SCV-07 at 100 ug/kg on days −1 to 16 showed significant improvement relative to controls on day 14 (P=0.025).

TABLE 3

Chi-square analysis of the total number of days the animals in each group spent with a score of three or more. This statistic is a measure of severity of ulceration, a clinically important outcome.

| Group | Days >=3 | Days <3 | Total Days | % Days >=3 | Chi Sq v control | P Value |
| --- | --- | --- | --- | --- | --- | --- |
| Control | 90 | 102 | 192 | 46.9 | — | — |
| SCV-07 1 ug/kg sc Days −1 to 16 | 90 | 102 | 192 | 46.9 | 0.0105 | 0.919 |
| SCV-07 10 ug/kg sc Days −1 to 16 | 72 | 120 | 192 | 37.5 | 3.0860 | 0.079 |
| SCV-07 100 ug/kg sc Days −1 to 16 | 68 | 124 | 192 | 35.4 | 4.7420 | 0.029 |

TABLE 4

The significance of group differences observed in daily mucositis scores was determined using the Mann-Whitney rank sum test. This nonparametric statistic is appropriate for the visual mucositis scoring scale. The p values for each calculation are shown. Significant improvements are shown underlined.

| Group Comparison | Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Control vs SCV-07 1 ug/kg Days −1 to 16 | 0.555 | 0.775 | 0.069 | 0.531 | 0.234 | 0.145 | 0.557 | 0.373 | 0.230 | 0.558 | 0.554 | 0.733 |
| Control vs SCV-07 10 ug/kg Days −1 to 16 | 0.985 | 0.775 | 0.372 | 0.554 | 0.117 | 0.265 | 0.374 | 0.116 | <u>0.024</u> | 0.316 | 0.608 | 0.361 |
| Control vs SCV-07 100 ug/kg Days −1 to 16 | 0.555 | 0.985 | 0.776 | 0.261 | <u>0.025</u> | 0.061 | 0.112 | 0.100 | 0.461 | 0.192 | 0.484 | 0.531 |

Conclusions

1. There was no evidence of any toxicity from SCV-07 in this study based on the observations of mortality and weight gain.
2. Animals treated with SCV-07 at 10 ug/kg on days −1 to 16 showed a statistically significant reduction in mucositis scores on day 22 (P=0.024) that was dose related.
3. Animals treated with SCV-07 at 100 ug/kg on days −1 to 16 showed a statistically significant reduction in mucositis scores on day 14 (P=0.025), in addition to a statistically significant reduction in the number of animal days with a score of 3 or higher (P=0.029).
4. A favorable dose-dependent effect of SCV-07 on the severity and course of mucositis was seen. Increasing the dosing frequency or doubling the single daily dose might enhance the effects noted.

APPENDICES

Appendix 1—Animal Weights

| Group | Animal | DAY | | | | | | | | | | | | | | | |
|---|---|---|---|---|---|---|---|---|---|---|---|---|---|---|---|---|---|
| | | −1 | 0 | 1 | 2 | 3 | 4 | 5 | 6 | 7 | 8 | 9 | 10 | 11 | 12 | 13 | 14 |
| 1 | 1 | 77 | 80 | 78 | 83 | 85 | 86 | 91 | 92 | 96 | 96 | 98 | 97 | 102 | 102 | 101 | 102 |
| 1 | 2 | 87 | 90 | 92 | 97 | 99 | 101 | 106 | 110 | 113 | 119 | 118 | 119 | 124 | 125 | 125 | 127 |
| 1 | 3 | 89 | 92 | 91 | 96 | 99 | 102 | 107 | 108 | 113 | 115 | 111 | 118 | 126 | 126 | 122 | 123 |
| 1 | 4 | 81 | 82 | 82 | 86 | 87 | 89 | 94 | 96 | 96 | 99 | 102 | 101 | 107 | 107 | 106 | 106 |
| 1 | 5 | 83 | 86 | 86 | 90 | 89 | 91 | 94 | 101 | 99 | 101 | 106 | 102 | 108 | 108 | 108 | 109 |
| 1 | 6 | 82 | 85 | 87 | 92 | 94 | 96 | 99 | 104 | 106 | 106 | 112 | 108 | 110 | 110 | 111 | 110 |
| 1 | 7 | 82 | 93 | 93 | 98 | 102 | 104 | 109 | 113 | 115 | 117 | 120 | 119 | 124 | 127 | 126 | 125 |
| 1 | 8 | 88 | 80 | 79 | 83 | 84 | 86 | 92 | 92 | 97 | 98 | 100 | 100 | 103 | 105 | 104 | 105 |
| 2 | 9 | 78 | 96 | 98 | 100 | 101 | 103 | 109 | 111 | 114 | 116 | 118 | 117 | 122 | 123 | 122 | 123 |
| 2 | 10 | 94 | 86 | 86 | 89 | 91 | 94 | 97 | 99 | 99 | 102 | 104 | 104 | 109 | 110 | 110 | 110 |
| 2 | 11 | 93 | 80 | 79 | 84 | 88 | 90 | 91 | 95 | 96 | 101 | 101 | 100 | 104 | 105 | 104 | 107 |
| 2 | 12 | 79 | 83 | 83 | 86 | 86 | 89 | 94 | 98 | 100 | 103 | 104 | 102 | 105 | 107 | 109 | 111 |
| 2 | 13 | 82 | 86 | 88 | 91 | 93 | 95 | 100 | 105 | 103 | 105 | 107 | 106 | 111 | 114 | 112 | 116 |
| 2 | 14 | 84 | 86 | 88 | 91 | 93 | 96 | 100 | 101 | 104 | 105 | 107 | 106 | 111 | 114 | 111 | 112 |
| 2 | 15 | 79 | 80 | 81 | 84 | 84 | 86 | 91 | 94 | 94 | 97 | 99 | 98 | 105 | 110 | 108 | 110 |
| 2 | 16 | 79 | 81 | 78 | 83 | 84 | 87 | 89 | 93 | 94 | 98 | 100 | 97 | 102 | 105 | 104 | 106 |
| 3 | 17 | 81 | 83 | 84 | 87 | 89 | 92 | 96 | 98 | 100 | 102 | 104 | 103 | 111 | 112 | 111 | 111 |
| 3 | 18 | 87 | 90 | 91 | 94 | 98 | 100 | 105 | 107 | 108 | 111 | 112 | 113 | 117 | 120 | 118 | 115 |
| 3 | 19 | 85 | 87 | 87 | 90 | 92 | 93 | 97 | 98 | 101 | 103 | 105 | 104 | 109 | 109 | 109 | 103 |
| 3 | 20 | 76 | 76 | 76 | 79 | 82 | 84 | 89 | 90 | 92 | 96 | 96 | 96 | 101 | 101 | 100 | 102 |
| 3 | 21 | 90 | 93 | 93 | 96 | 98 | 100 | 103 | 106 | 108 | 109 | 111 | 110 | 113 | 117 | 113 | 110 |
| 3 | 22 | 91 | 95 | 94 | 98 | 100 | 103 | 108 | 109 | 112 | 114 | 116 | 115 | 121 | 124 | 122 | 122 |
| 3 | 23 | 86 | 91 | 91 | 95 | 98 | 100 | 105 | 101 | 109 | 113 | 114 | 115 | 121 | 121 | 121 | 121 |
| 3 | 24 | 91 | 95 | 96 | 100 | 104 | 106 | 113 | 116 | 115 | 120 | 122 | 124 | 129 | 130 | 130 | 129 |
| 4 | 25 | 84 | 87 | 87 | 91 | 93 | 96 | 100 | 103 | 105 | 109 | 111 | 110 | 117 | 119 | 117 | 117 |
| 4 | 26 | 87 | 91 | 98 | 94 | 95 | 98 | 101 | 104 | 105 | 109 | 112 | 111 | 119 | 117 | 115 | 118 |
| 4 | 27 | 97 | 101 | 101 | 108 | 110 | 111 | 119 | 123 | 124 | 127 | 132 | 133 | 137 | 138 | 134 | 139 |
| 4 | 28 | 88 | 95 | 93 | 98 | 101 | 103 | 101 | 115 | 118 | 118 | 124 | 121 | 130 | 131 | 132 | 139 |
| 4 | 29 | 86 | 90 | 86 | 92 | 97 | 100 | 104 | 106 | 108 | 111 | 114 | 115 | 120 | 123 | 121 | 125 |
| 4 | 30 | 84 | 88 | 89 | 92 | 95 | 99 | 106 | 109 | 111 | 115 | 120 | 118 | 129 | 131 | 127 | 132 |
| 4 | 31 | 95 | 100 | 99 | 106 | 109 | 111 | 118 | 119 | 122 | 126 | 127 | 128 | 136 | 137 | 133 | 138 |
| 4 | 32 | 85 | 87 | 89 | 94 | 94 | 97 | 105 | 106 | 108 | 110 | 114 | 113 | 118 | 121 | 118 | 120 |

| Group | Animal | DAY | | | | | | | | | | | | | |
|---|---|---|---|---|---|---|---|---|---|---|---|---|---|---|---|
| | | 15 | 16 | 17 | 18 | 19 | 20 | 21 | 22 | 23 | 24 | 25 | 26 | 27 | 28 |
| 1 | 1 | 101 | 103 | 100 | 107 | 109 | 109 | 112 | 113 | 116 | 115 | 119 | 119 | 121 | 123 |
| 1 | 2 | 126 | 125 | 130 | 134 | 140 | 141 | 143 | 146 | 149 | 149 | 153 | 152 | 154 | 158 |

-continued

| Group | Animal | | | | | | | | | | | | | |
|---|---|---|---|---|---|---|---|---|---|---|---|---|---|---|
| 1 | 3 | 122 | 129 | 123 | 130 | 134 | 135 | 137 | 140 | 142 | 147 | 147 | 148 | 149 | 152 |
| 1 | 4 | 106 | 109 | 106 | 115 | 116 | 117 | 119 | 121 | 126 | 125 | 130 | 127 | 131 | 136 |
| 1 | 5 | 108 | 110 | 109 | 118 | 119 | 121 | 122 | 124 | 129 | 128 | 131 | 132 | 135 | 137 |
| 1 | 6 | 111 | 113 | 113 | 120 | 121 | 121 | 124 | 127 | 128 | 130 | 135 | 135 | 138 | 140 |
| 1 | 7 | 127 | 128 | 127 | 137 | 139 | 141 | 143 | 144 | 149 | 149 | 153 | 153 | 156 | 159 |
| 1 | 8 | 105 | 108 | 106 | 114 | 117 | 117 | 119 | 123 | 126 | 126 | 129 | 129 | 132 | 135 |
| 2 | 9 | 123 | 129 | 126 | 133 | 136 | 137 | 139 | 141 | 143 | 143 | 147 | 148 | 150 | 152 |
| 2 | 10 | 110 | 115 | 114 | 118 | 121 | 120 | 122 | 125 | 128 | 129 | 131 | 134 | 135 | 138 |
| 2 | 11 | 111 | 112 | 108 | 117 | 118 | 118 | 121 | 123 | 124 | 124 | 129 | 131 | 134 | 135 |
| 2 | 12 | 111 | 116 | 112 | 119 | 123 | 122 | 123 | 124 | 130 | 131 | 137 | 133 | 139 | 138 |
| 2 | 13 | 117 | 121 | 117 | 125 | 127 | 128 | 131 | 132 | 135 | 133 | 140 | 140 | 144 | 147 |
| 2 | 14 | 112 | 115 | 113 | 119 | 120 | 122 | 123 | 125 | 126 | 128 | 131 | 131 | 133 | 136 |
| 2 | 15 | 109 | 113 | 108 | 116 | 118 | 119 | 120 | 123 | 125 | 126 | 130 | 130 | 133 | 137 |
| 2 | 16 | 106 | 111 | 109 | 115 | 118 | 120 | 121 | 121 | 126 | 125 | 129 | 131 | 132 | 135 |
| 3 | 17 | 112 | 116 | 116 | 122 | 124 | 123 | 122 | 123 | 126 | 126 | 132 | 132 | 133 | 137 |
| 3 | 18 | 110 | 102 | 107 | 113 | 115 | 117 | 119 | 121 | 122 | 126 | 128 | 130 | 133 | 137 |
| 3 | 19 | 101 | 111 | 102 | 107 | 111 | 112 | 113 | 115 | 117 | 120 | 122 | 123 | 120 | 129 |
| 3 | 20 | 105 | 107 | 104 | 113 | 116 | 115 | 119 | 119 | 122 | 122 | 127 | 127 | 131 | 134 |
| 3 | 21 | 111 | 115 | 111 | 117 | 119 | 120 | 120 | 123 | 125 | 125 | 128 | 129 | 132 | 135 |
| 3 | 22 | 120 | 124 | 123 | 130 | 132 | 134 | 136 | 137 | 140 | 139 | 145 | 145 | 149 | 151 |
| 3 | 23 | 121 | 124 | 125 | 132 | 137 | 139 | 139 | 141 | 145 | 146 | 146 | 153 | 155 | 137 |
| 3 | 24 | 131 | 134 | 133 | 142 | 146 | 147 | 149 | 150 | 155 | 155 | 160 | 161 | 165 | 167 |
| 4 | 25 | 116 | 118 | 118 | 124 | 124 | 124 | 123 | 124 | 124 | 124 | 127 | 127 | 129 | 131 |
| 4 | 26 | 117 | 120 | 119 | 126 | 126 | 129 | 132 | 134 | 135 | 135 | 138 | 140 | 143 | 147 |
| 4 | 27 | 138 | 141 | 142 | 151 | 153 | 154 | 156 | 157 | 161 | 167 | 167 | 175 | 169 | 172 |
| 4 | 28 | 138 | 143 | 143 | 152 | 155 | 159 | 159 | 162 | 164 | 167 | 173 | 169 | 175 | 182 |
| 4 | 29 | 126 | 129 | 130 | 137 | 139 | 141 | 143 | 147 | 151 | 150 | 156 | 158 | 160 | 166 |
| 4 | 30 | 133 | 136 | 136 | 144 | 149 | 148 | 150 | 154 | 156 | 160 | 165 | 165 | 167 | 168 |
| 4 | 31 | 139 | 142 | 140 | 148 | 151 | 152 | 153 | 156 | 156 | 157 | 164 | 163 | 164 | 166 |
| 4 | 32 | 119 | 125 | 125 | 131 | 134 | 136 | 137 | 138 | 141 | 142 | 147 | 147 | 149 | 152 |

Appendix 2—Mucositis Scores

| Group | Animal | \multicolumn{12}{c}{DAYS} |
|---|---|---|---|---|---|---|---|---|---|---|---|---|---|
| | | 6 | 8 | 10 | 12 | 14 | 16 | 18 | 20 | 22 | 24 | 26 | 28 |
| 1 | 1 | 0 | 1 | 1 | 1 | 2 | 3 | 4 | 4 | 3 | 2 | 2 | 1 |
| 1 | 2 | 0 | 1 | 1 | 1 | 2 | 3 | 4 | 3 | 3 | 3 | 2 | 1 |
| 1 | 3 | 0 | 1 | 2 | 2 | 3 | 3 | 4 | 3 | 2 | 2 | 2 | 1 |
| 1 | 4 | 1 | 1 | 1 | 2 | 2 | 3 | 4 | 3 | 3 | 3 | 2 | 1 |
| 1 | 5 | 0 | 1 | 1 | 2 | 2 | 3 | 4 | 3 | 2 | 2 | 1 | 1 |
| 1 | 6 | 0 | 0 | 1 | 2 | 3 | 4 | 3 | 3 | 3 | 3 | 3 | 1 |
| 1 | 7 | 0 | 0 | 1 | 3 | 2 | 3 | 4 | 3 | 3 | 2 | 1 | 1 |
| 1 | 8 | 0 | 0 | 1 | 2 | 3 | 4 | 4 | 3 | 2 | 2 | 1 | 1 |
| 2 | 9 | 0 | 1 | 2 | 2 | 3 | 4 | 4 | 3 | 3 | 3 | 2 | 0 |
| 2 | 10 | 1 | 1 | 1 | 2 | 2 | 3 | 4 | 3 | 3 | 3 | 3 | 1 |
| 2 | 11 | 0 | 1 | 1 | 2 | 3 | 3 | 4 | 3 | 3 | 2 | 2 | 1 |
| 2 | 12 | 0 | 0 | 2 | 3 | 3 | 3 | 4 | 3 | 2 | 3 | 2 | 1 |
| 2 | 13 | 1 | 1 | 3 | 2 | 3 | 3 | 3 | 2 | 2 | 2 | 2 | 1 |
| 2 | 14 | 0 | 1 | 1 | 2 | 2 | 3 | 4 | 3 | 3 | 3 | 2 | 1 |
| 2 | 15 | 0 | 1 | 1 | 1 | 2 | 3 | 4 | 4 | 2 | 2 | 2 | 1 |
| 2 | 16 | 0 | 1 | 1 | 2 | 2 | 3 | 4 | 3 | 2 | 2 | 1 | 1 |
| 3 | 17 | 1 | 1 | 1 | 2 | 2 | 3 | 4 | 3 | 2 | 2 | 2 | 1 |
| 3 | 18 | 0 | 0 | 1 | 2 | 3 | 3 | 4 | 3 | 2 | 2 | 2 | 2 |
| 3 | 19 | 1 | 1 | 1 | 2 | 3 | 3 | 4 | 3 | 2 | 3 | 2 | 1 |
| 3 | 20 | 1 | 1 | 1 | 2 | 2 | 3 | 3 | 2 | 1 | 2 | 1 | 1 |
| 3 | 21 | 1 | 1 | 1 | 2 | 2 | 3 | 4 | 3 | 3 | 3 | 3 | 1 |
| 3 | 22 | 0 | 1 | 1 | 1 | 2 | 3 | 4 | 3 | 2 | 2 | 2 | 1 |
| 3 | 23 | 0 | 1 | 1 | 2 | 2 | 3 | 4 | 3 | 1 | 2 | 2 | 1 |
| 3 | 24 | 1 | 1 | 1 | 2 | 2 | 3 | 3 | 3 | 2 | 2 | 1 | 0 |
| 4 | 25 | 0 | 1 | 1 | 1 | 2 | 3 | 4 | 4 | 4 | 3 | 3 | 1 |
| 4 | 26 | 0 | 1 | 1 | 2 | 2 | 3 | 4 | 3 | 3 | 2 | 2 | 1 |
| 4 | 27 | 0 | 0 | 2 | 2 | 2 | 3 | 4 | 3 | 3 | 2 | 3 | 2 |
| 4 | 28 | 1 | 1 | 1 | 2 | 2 | 3 | 3 | 3 | 2 | 2 | 3 | 3 |
| 4 | 29 | 0 | 0 | 1 | 2 | 3 | 3 | 4 | 3 | 2 | 2 | 1 | 1 |
| 4 | 30 | 1 | 1 | 1 | 2 | 2 | 2 | 2 | 1 | 2 | 2 | 1 | 1 |
| 4 | 31 | 0 | 0 | 1 | 2 | 2 | 3 | 3 | 2 | 1 | 2 | 1 | 1 |
| 4 | 32 | 1 | 0 | 1 | 2 | 3 | 4 | 4 | 3 | 3 | 2 | 1 | 1 |

Example 2

A Second Study of SCV-07 in the Treatment of Oral Mucositis Induced by Acute Radiation in Hamsters The objective of this study was to conduct a preliminary evaluation of the efficacy of SCV-07 in the treatment of oral mucositis using an acute radiation induced hamster model of the disease. SCV-07 was given at doses of 1 mg/kg or 100 µg/kg once or twice daily by sub-cutaneous injection for 22 days, starting one day before radiation and continuing until day 20 after radiation. No deaths were observed in any of the treatment groups and there were statistically significant increases in growth rate, suggesting that SCV-07 was well tolerated at these doses, and may actually reduce the weight loss associated with mucositis. Control hamsters had a mucositis score of 3 or higher on 28.1% of the animal days evaluated in this study. Animals treated with SCV-07 at 100 µg/kg once daily on days −1 to 20 showed a statistically significant reduction in the number of animals days with a score of 3 or higher to 6.3% (P<0.001), and a statistically significant reduction in individual daily scores on days 14 (P=0.011), 16 (P=0.002) and 18 (P=0.001). Animals treated with SCV-07 at 100 µg/kg twice daily on days −1 to 20 showed a statistically significant reduction in the number of animals days with a score of 3 or higher to 8.9% (P<0.001), and a statistically significant reduction in individual daily scores on days 18 (P<0.001) and 20 (P=0.003). Animals treated with SCV-07 at 1 mg/kg twice daily on days −1 to 20 showed a statistically significant reduction in the number of animals days with a score of 3 or higher to 12.5% (P<0.001), and a statistically significant reduction in individual daily scores on days 16 (P=0.043) 18 (P=0.009) and 20 (P=0.007). Animals treated with SCV-07 at 1 mg/kg twice daily on days −1 to 20 did not show any significant reduction in mucositis scores. There was no statistically significant difference in the number of animal days with a score of 3 or higher between the group treated with SCV-07 at 100 µg/kg once daily and the group treated with SCV-07 at 1 mg/kg twice daily (P=0.054). When individual daily scores were compared between these two groups, a single day of significant difference was observed on day 14 (P=0.005). These observations suggest that treatment with SCV-07 at 100 µg/kg once daily is very close to being significantly better that treatment with SCV-07 at 1 mg/kg twice daily. This observation suggests that 100 µg/kg once daily is the dose closest to the optimal dose of the doses tested in this study and in the prior study SCI-01.

Introduction 1.1 Background

Oral ulcerative mucositis is a common, painful, dose-limiting toxicity of drug and radiation therapy for cancer. The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of patients receiving anti-neoplastic drug therapy. The frequency and severity are significantly greater among patients who are treated with induction therapy for leukemia or with many of the conditioning regimens for bone marrow transplant. Among these individuals, moderate to severe mucositis is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through three stages:
1. Inflammation accompanied by painful mucosal erythema, which can respond to local anesthetics.
2. Painful ulceration with pseudomembrane formation and, in the case of myelosuppressive treatment, potentially life-threatening sepsis, requiring antimicrobial therapy. Pain is often of such intensity as to require parenteral narcotic analgesia.
3. Spontaneous healing, occurring about 2-3 weeks after cessation of anti-neoplastic therapy.

Standard therapy for mucositis is predominantly palliative, including application of topical analgesics such as lidocaine and/or systemic administration of narcotics and antibiotics. Currently, there is only one approved treatment for oral mucositis, Kepivance (Palifermin), which is only approved for the treatment of oral mucositis in patients undergoing conditioning regimens prior to hematopoetic stem cell transplantation for the treatment of hematologic malignancies.

The complexity of mucositis as a biological process has only been recently appreciated. It has been suggested that the condition represents a sequential interaction of oral mucosal cells and tissues, reactive oxygen species, pro-inflammatory cytokines, mediators of apoptosis and local factors such as saliva and the oral micro biota. While epithelial degeneration and breakdown ultimately result in mucosal ulceration, it appears that the early changes associated with radiation-induced mucosal toxicity occur within the endothelium, and connective tissue of the submucosa. Electron microscopic evaluation of mucosa within 1 week of radiation shows damage to both endothelium and connective tissue, but not epithelium. Such injury is likely mediated by free radical formation. It appears that the overall mechanism for mucositis development is similar for both radiation and chemotherapy.

1.2 Acute Radiation Model

The acute radiation model in hamsters, developed by the Principle Investigator, has proven to be an accurate, efficient and cost-effective technique to provide a preliminary evaluation of anti-mucositis compounds. The course of mucositis in this model is well defined and results in peak scores approximately 14-16 Days following radiation. The acute model has little systemic toxicity, resulting in few hamster deaths, thus permitting the use of smaller groups (N=7-8) for initial efficacy studies. It has also been used to study specific mechanistic elements in the pathogenesis of mucositis. Molecules that show efficacy in the acute radiation model may be further evaluated in the more complex models of fractionated radiation, chemotherapy, or concomitant therapy.

In this study, an acute radiation dose of 40 Gy on day 0 was administered. Clinically significant mucositis was observed on days 12 through 28.

2. Study Objective and Summary 2.1 Study Objective

The objective of this study was to evaluate the effect of SCV-07, administered by sub-cutaneous injection on different schedules between the day before radiation and the twentieth day after radiation, on the frequency, severity and duration of oral mucositis induced by acute radiation. A previous study with SCV-07 (Study SCI-01, Example 1), had indicated some activity against mucositis at a dose of 100 µg/kg, given once daily from day −1 to day 16. In this study, SCV-07 was dosed at 100 µg/kg and 1 mg/kg once or twice daily from day −1 to day 20, to see if the partial effect seen in the previous study could be extended.

2.2 Study Summary

Forty (40) Syrian Golden Hamsters were given an acute radiation dose of 40 Gy directed to their left buccal cheek pouch on day 0. Test material SCV-07 was given by sub-cutaneous injection at 100 µg/kg or 1 mg/kg once or twice daily. Dosing began one day before radiation (day −1) and continued until day 20. Mucositis was evaluated clinically starting on day 6, and continuing on alternate days until day 28.

3. Evaluation 3.1 Mucositis Evaluation

The grade of mucositis was scored, beginning day 6, and for every second day thereafter, through and including day 28. The effect on mucositis of each drug treatment compared to placebo was assessed according to the following parameters:
3.1.1 The Difference in the Number of Days Hamsters in Each Group have Ulcerative (Score ≧3) Mucositis.

On each evaluation day, the number of animals with a blinded mucositis score of ≧3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores ≧3) when compared to the control group. This same test was also used to evaluate differences between different drug treatment groups.

3.1.2 Rank Sum Differences in Daily Mucositis Scores.

For each evaluation day the scores of the control group were compared to those of the treated groups using non-parametric rank sum analysis. Treatment success was considered as a statistically significant lowering of scores in the treated group on 2 or more days from day 6 to day 28.

3.2 Weights and Survival

All animals were weighed daily and their survival recorded, in order to assess possible differences in animal weight among treatment groups as an indication for mucositis severity and/or possible toxicity resulting from the treatments.

4. Study Design

Forty Syrian Golden Hamsters were divided into five (5) groups of eight (8) animals each. All animals received a single dose of acute radiation of 40 Gy directed to their left buccal cheek pouch on day 0. This was accomplished by anesthetizing the animals and everting the left buccal pouch, while protecting the rest of the animals with a lead shield. Test materials were given by sub-cutaneous injection once daily as detailed in Table 5. Mucositis was evaluated clinically starting on Day 6, and continuing on alternate days until day 28.

TABLE 5

SCI-02. Study Design

| Group Number | Number of Animals | Treatment | Treatment Schedule* | Volume (mL) |
|---|---|---|---|---|
| 1 | 8 males | Vehicle (PBS), sc, qd | Day −1 to 20 | Adjust per body weight |
| 2 | 8 males | SCV-07, sc, qd 100 μg/kg, | Day −1 to 20 | Adjust per body weight |
| 3 | 8 males | SCV-07, sc, bid 100 μg/kg, | Day −1 to 20 | Adjust per body weight |
| 4 | 8 males | SCV-07, sc, qd 1.0 mg/kg | Day −1 to 20 | Adjust per body weight |
| 5 | 8 males | SCV-07, sc, bid 1.0 mg/kg | Day −1 to 20 | Adjust per body weight |

*The dose on day 0 was performed 30 minutes prior to radiation

5. Material and Methods

5.1 Location of Study Performance

The study was performed at Biomodels AAALAC accredited facility in Watertown Mass. Approval for this study was obtained from Biomodels IACUC.

5.2 Animals

Male LVG Syrian Golden Hamsters (Charles River Laboratories), aged 5 to 6 weeks, with average body weight of 81.9 g at study commencement, were used. Animals were individually numbered using an ear punch and housed in small groups of 8 animals per cage. Animals were acclimatized prior to study commencement. During this period of 5 days, the animals were observed daily in order to reject animals that presented in poor condition.

5.3 Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained.

5.4 Diet

Animals were fed with a Purina Labdiet® 5061 rodent diet and water was provided ad libitum.

5.5 Animal Randomization and Allocations

Animals were randomly and prospectively divided into five (5) treatment groups prior to irradiation. Each animal was identified by an ear punch corresponding to an individual number. For more consistent identification, ear punch numbering was used rather than tagging, since tags may become dislodged during the course of the study. A cage card was used to identify each cage or label marked with the study number (SCI-02), treatment group number and animal numbers.

5.6 Sub-Cutaneous Dosing and Drug Application

The test compound, SCV-07 was provided as a powder and dissolved in sterile PBS immediately prior to administration. Three dilutions were prepared: 100 μg/mL, 10 μg/mL and 1 μg/mL. Drug was given in a volume of 0.1 mL per 100 g body weight, with the appropriate dilution of SCV-07 for each group, using a tuberculin syringe with a 27G needle. Injections were given subcutaneously to the back or abdomen.

5.7 Mucositis Induction

Mucositis was induced using a standardized acute radiation protocol. A single dose of radiation (40 Gy/dose) was administered to all animals on day 0. Radiation was generated with a 160 kilovolt potential (15-ma) source at a focal distance of 30 cm, hardened with a 0.35 mm Cu filtration system. Irradiation targeted the left buccal pouch mucosa at a rate of 3.2 Gy/minute. Prior to irradiation, animals were anesthetized with an intraperitoneal injection of Ketamine (160 mg/kg) and Xylazine (8 mg/kg). The left buccal pouch was everted, fixed and isolated using a lead shield to protect all other parts of the hamster's body.

5.8 Mucositis Scoring

The mucositis score, weight change and survival were measured throughout the study as described above. For the evaluation of mucositis, the animals were anesthetized with an inhalation anesthetic, and the left pouch everted. Mucositis was scored visually by comparison to a validated photographic scale, ranging from 0 for normal, to 5 for severe ulceration (clinical scoring). In descriptive terms, this scale is defined as follows:

TABLE 6

SCI-02: Mucositis Scoring.

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

6. Results and Discussion

6.1 Survival

No deaths were observed during the course of this study.

6.2 Weight Change

The mean daily percent weight change data was evaluated. The saline treated control hamsters gained an average of 44.1% of their starting weight during the study. Hamsters in the group receiving SCV-07 100 μg/kg once daily on days −1 to 20 gained an average of 49.9% of their starting weight during the study. Hamsters in the group receiving SCV-07 at 100 μg/kg twice daily on days −1 to 20 gained an average of 61.3% of their starting weight during the study. Hamsters in the group receiving SCV-07 at 1 mg/kg once daily on days −1 to 20 gained an average of 63.4% of their starting weight during the study. Hamsters in the group receiving SCV-07 at 1 mg/kg twice daily on days −1 to 20 gained an average of 69.1% of their starting weight during the study. The significance of these differences was evaluated by calculating the area-under-the-curve (AUC) for the weight gain of each animal, and then comparing the different treatment groups using a One-Way ANOVA test. The results of this analysis indicated that there were significant differences between the SCV-07 treated groups and the control group (P=0.012). The groups treated with SCV-07 100 μg/kg twice daily, 1 mg/kg once and twice daily all had significantly greater weight gain than the saline controls (P=0.014, P=0.009 and P=0.004 respectively).

6.3 Mucositis (Tables 7 & 8)

Mean daily mucositis scores for each group are were determined. In the saline treated control group, peak levels of mucositis were seen on day 18, when the mean score reached 3.0. The group receiving SCV-07 at 100 μg/kg once daily from day −1 to 20 had a peak mean mucositis score of 2.2 on day 16. The group receiving SCV-07 at 100 μg/kg twice daily from day −1 to 20 had a peak mean mucositis score of 2.5 which occurred on days 14 and 16. The group receiving SCV-07 at 1 mg/kg once daily from day −1 to 20 had a peak mean mucositis score of 2.9 on day 14. The group receiving SCV-07 at 1 mg/kg twice daily from day −1 to 20 had a peak mean mucositis score of 2.6 on day 14. The significance of the differences observed between the different treatment groups was evaluated by calculating the number of days with a score of 3 or higher for each group and comparing these numbers using a chi-squared ($\square^2$) test. The results of this analysis are shown in Table 7. The hamsters in the saline treated control group had a score of 3 or higher on 28.1% of the animal days evaluated. In the group receiving SCV-07 at 100 μg/kg once daily from day −1 to 20, a mucositis score of 3 or higher was observed on 6.3% of the animals days evaluated, which was statistically significantly different that the controls (P<0.001). The hamsters in the groups treated with SCV-07 at 100 μg/kg twice daily on days −1 to 20 had a score of 3 or higher on 8.9% of animal days respectively, which was statistically significantly different from the controls (P<0.001). The group treated with SCV-07 at 1 mg/kg once daily on days −1 to 20 had a score of 3 or higher on 28.1% of animal days, which was not significantly different from controls (P=1.000). The group treated with SCV-07 at 1 mg/kg twice daily on days −1 to 20 had a score of 3 or higher on 12.5% of animal days, which was significantly different from controls (P<0.001). There was no statistically significant difference in the number of animal days with a score of 3 or higher between the group treated with SCV-07 at 100 μg/kg once daily and the group treated with SCV-07 at 1 mg/kg twice daily (P=0.054).

A further analysis of the mucositis scores was performed using the Mann-Whitney rank sum analysis to compare the scores for each group on each day. The results of this analysis are shown in Table 8. In this analysis, 2 days of significant reduction in the mucositis score are generally required before it is regarded as meaningful reduction in mucositis. The group treated with SCV-07 at 100 μg/kg once daily on days −1 to 20 showed statistically significant improvement on days 14 (P=0.011), 16 (P=0.002) and 18 (P=0.001) of the study relative to the saline controls. The group treated with SCV-07 at 100 μg/kg twice daily on days −1 to 20 showed significant improvement relative to controls on days 18 (P<0.001) and 20 (P=0.003). The group treated with SCV-07 at 1 mg/kg once daily on days −1 to 20 showed no significant improvement in mucositis on any day of the study relative to controls. The group treated with SCV-07 at 1 mg/kg twice daily on days −1 to 20 showed significant improvement relative to controls on days 16 (P=0.043) 18 (P=0.009) and 20 (P=0.007). A comparison between the group treated with SCV-07 at 100 μg/kg once daily and the group treated with SCV-07 at 1 mg/kg twice daily showed a single day of statistically significant difference on day 14 (P=0.005).

TABLE 7

SCI-02. Chi-square analysis of the total number of days the animals in each group spent with a score of three or more. This statistic is a measure of severity of ulceration, a clinically important outcome.

| Group | Days >=3 | Days <3 | Total Days | % Days >=3 | Chi Sq v control | P Value |
|---|---|---|---|---|---|---|
| Vehicle (PBS), qd, sc | 54 | 138 | 192 | 28.1 | — | — |
| SCV-07 100 ug/kg, qd, sc | 12 | 180 | 192 | 6.3 | 27.828 | <0.001 |
| SCV-07 100 ug/kg, bid, sc | 17 | 175 | 192 | 8.9 | 21.4010 | <0.001 |
| SCV-07 1 mg/kg, qd, sc | 54 | 138 | 192 | 28.1 | 0.0000 | 1.000 |
| SCV-07 1 mg/kg, bid, sc | 24 | 168 | 192 | 12.5 | 12.7360 | <0.001 |

7. Conclusions

1. There was no evidence of any toxicity from SCV-07 in this study based on the observations of mortality and weight gain.

2. The groups treated with SCV-07 at 100 μg/ml twice daily or SCV-07 1 mg/ml once or twice daily showed significant increases in weight gain relative to the saline controls (P=0.014, P=0.009 and P=0.004 respectively).

3. Animals treated with SCV-07 at 100 μg/kg once daily on days −1 to 20 showed a statistically significant reduction in the number of animals days with a score of 3 or higher (P<0.001), and a statistically significant reduction in individual daily scores on days 14 (P=0.011), 16 (P=0.002) and 18 (P=0.001).

4. Animals treated with SCV-07 at 100 μg/kg twice daily on days −1 to 20 showed a statistically significant reduction in the number of animals days with a score of 3 or higher (P<0.001), and a statistically significant reduction in individual daily scores on days 18 (P<0.001) and 20 (P=0.003).

5. Animals treated with SCV-07 at 1 mg/kg twice daily on days −1 to 20 showed a statistically significant reduction in the number of animals days with a score of 3 or higher (P<0.001), and a statistically significant reduction in individual daily scores on days 16 (P=0.043) 18 (P=0.009) and 20 (P=0.007).

6. Animals treated with SCV-07 at 1 mg/kg twice daily on days −1 to 20 did not show any significant reduction in mucositis scores.

7. There was no statistically significant difference in the number of animal days with a score of 3 or higher between the group treated with SCV-07 at 100 μg/kg once daily and the group treated with SCV-07 at 1 mg/kg twice daily (P=0.054). When individual daily scores were compared between these two groups, a single day of significant difference was observed on day 14 (P=0.005).

These observations suggest that treatment with SCV-07 at 100 μg/kg once daily is very close to being significantly better that treatment with SCV-07 at 1 mg/kg twice daily.

TABLE 8

SCI-02. The significance of group differences observed in daily mucositis scores was determined using the Mann-Whitney rank sum test. This nonparametric statistic is appropriate for the visual mucositis scoring scale. The p values for each calculation are shown. Significant improvements are shown underlined.

| Group Comparison | Day 6 | 8 | 10 | 12 | 14 | 16 | 18 | 20 | 22 | 24 | 26 | 28 |
|---|---|---|---|---|---|---|---|---|---|---|---|---|
| Control vs SCV-7 100 ug/kg, qd, sc Days −1 to 20 | 0.558 | 0.985 | 0.985 | 0.425 | <u>0.011</u> | <u>0.002</u> | <u>0.001</u> | 0.092 | 0.413 | 0.436 | 0.555 | 0.374 |
| Control vs SCV-7 100 ug/kg, bid, sc Days −1 to 20 | 0.558 | 0.554 | 0.985 | 0.581 | 0.664 | 0.204 | <u><0.001</u> | <u>0.003</u> | 0.279 | 0.805 | 0.775 | 0.558 |
| Control vs SCV-7 1 mg/kg, qd, sc Days −1 to 20 | 0.233 | 0.985 | 0.985 | 0.775 | 0.218 | 0.662 | 0.116 | 0.405 | 0.404 | 0.298 | 0.774 | 0.895 |
| Control vs SCV-7 1 mg/kg, bid, sc Days −1 to 20 | 0.072 | 0.985 | 0.985 | 0.805 | 0.925 | <u>0.043</u> | <u>0.009</u> | <u>0.007</u> | 0.581 | 0.985 | 0.774 | 0.777 |
| SCV-7 100 ug/kg, qd, sc vs SCV-7 1 mg/kg, bid, sc Days −1 to 20 | 0.233 | 0.985 | 0.985 | 0.279 | <u>0.005</u> | 0.232 | 0.335 | 0.371 | 0.775 | 0.370 | 0.370 | 0.557 |

9. Appendices

9.1 Appendix 3—Animal Weights

| Group | Animal | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| 1 | 1 | 84.7 | 84.6 | 87 | 89 | 92 | 94 | 96 | 98 | 98 | 102 | 104 | 105 | 107 | 104 | 106 | 105 |
| 1 | 2 | 79.1 | 79 | 79 | 83 | 88 | 88 | 92 | 91 | 93 | 101 | 101 | 102 | 104 | 105 | 108 | 108 |
| 1 | 3 | 84.1 | 84.3 | 86 | 88 | 93 | 93 | 95 | 97 | 97 | 102 | 104 | 105 | 115 | 105 | 105 | 103 |
| 1 | 4 | 81.3 | 79.1 | 81 | 82 | 84 | 84 | 86 | 89 | 90 | 92 | 90 | 96 | 99 | 97 | 99 | 100 |
| 1 | 5 | 84.6 | 86.9 | 86 | 89 | 93 | 95 | 98 | 100 | 99 | 106 | 108 | 109 | 110 | 109 | 108 | 108 |
| 1 | 6 | 90.9 | 92.3 | 94 | 96 | 99 | 103 | 107 | 108 | 107 | 113 | 113 | 113 | 105 | 113 | 117 | 116 |
| 1 | 7 | 80.3 | 78.5 | 82 | 83 | 86 | 89 | 91 | 92 | 95 | 97 | 100 | 100 | 103 | 99 | 101 | 101 |
| 1 | 8 | 85.3 | 85.2 | 89 | 90 | 95 | 98 | 99 | 100 | 105 | 108 | 108 | 108 | 109 | 109 | 111 | 110 |
| 2 | 9 | 87.6 | 86.5 | 92 | 96 | 98 | 102 | 105 | 107 | 108 | 114 | 117 | 109 | 120 | 118 | 124 | 123 |
| 2 | 10 | 87.2 | 80.5 | 86 | 94 | 97 | 99 | 101 | 103 | 105 | 111 | 110 | 103 | 114 | 110 | 116 | 116 |
| 2 | 11 | 81.6 | 81.7 | 86 | 86 | 87 | 88 | 90 | 90 | 94 | 95 | 97 | 90 | 98 | 95 | 98 | 99 |
| 2 | 12 | 71.9 | 72.8 | 75 | 77 | 79 | 79 | 85 | 84 | 85 | 88 | 91 | 88 | 97 | 97 | 101 | 98 |
| 2 | 13 | 86.2 | 85.7 | 91 | 93 | 94 | 95 | 98 | 97 | 99 | 101 | 105 | 98 | 109 | 104 | 110 | 110 |
| 2 | 14 | 81.9 | 82.6 | 86 | 87 | 90 | 90 | 92 | 94 | 94 | 101 | 100 | 95 | 104 | 102 | 106 | 102 |
| 2 | 15 | 82.7 | 83.4 | 88 | 91 | 93 | 95 | 97 | 99 | 100 | 105 | 106 | 101 | 109 | 106 | 110 | 111 |
| 2 | 16 | 80.4 | 81.2 | 90 | 88 | 89 | 92 | 93 | 94 | 98 | 98 | 103 | 99 | 107 | 106 | 111 | 113 |
| 3 | 17 | 77.1 | 77.1 | 80 | 83 | 79 | 84 | 91 | 91 | 85 | 98 | 100 | 99 | 101 | 97 | 103 | 104 |
| 3 | 18 | 75 | 75.8 | 82 | 81 | 81 | 82 | 85 | 85 | 81 | 90 | 92 | 91 | 92 | 88 | 94 | 94 |
| 3 | 19 | 86.6 | 86.1 | 93 | 94 | 92 | 98 | 102 | 105 | 99 | 113 | 115 | 117 | 120 | 116 | 121 | 127 |
| 3 | 20 | 80.2 | 79.1 | 86 | 89 | 84 | 86 | 93 | 95 | 89 | 100 | 103 | 102 | 104 | 101 | 105 | 106 |
| 3 | 21 | 81.7 | 81 | 87 | 90 | 85 | 89 | 92 | 94 | 87 | 98 | 100 | 100 | 104 | 99 | 105 | 104 |
| 3 | 22 | 82 | 80.3 | 86 | 89 | 85 | 89 | 92 | 95 | 88 | 99 | 102 | 102 | 104 | 100 | 106 | 105 |
| 3 | 23 | 80.8 | 80.8 | 87 | 90 | 89 | 93 | 101 | 100 | 93 | 107 | 107 | 108 | 115 | 108 | 113 | 114 |
| 3 | 24 | 83 | 80.7 | 88 | 94 | 85 | 94 | 102 | 102 | 95 | 110 | 113 | 113 | 118 | 117 | 120 | 121 |
| 4 | 25 | 85.2 | 84.3 | 86 | 89 | 93 | 92 | 98 | 98 | 100 | 106 | 105 | 107 | 109 | 108 | 110 | 107 |
| 4 | 26 | 88.7 | 89.4 | 94 | 98 | 100 | 101 | 104 | 107 | 108 | 113 | 114 | 116 | 119 | 118 | 121 | 120 |
| 4 | 27 | 83.4 | 84.9 | 86 | 90 | 92 | 93 | 97 | 97 | 98 | 102 | 103 | 105 | 105 | 105 | 108 | 105 |
| 4 | 28 | 72.4 | 75.7 | 77 | 79 | 81 | 81 | 85 | 85 | 86 | 90 | 92 | 93 | 94 | 94 | 93 | 91 |
| 4 | 29 | 72.3 | 75.8 | 77 | 78 | 83 | 82 | 87 | 91 | 91 | 99 | 99 | 102 | 103 | 104 | 105 | 106 |
| 4 | 30 | 90.6 | 94 | 96 | 99 | 101 | 104 | 109 | 111 | 109 | 115 | 116 | 115 | 103 | 118 | 120 | 120 |
| 4 | 31 | 75.9 | 77.5 | 79 | 82 | 84 | 85 | 89 | 91 | 91 | 98 | 99 | 100 | 117 | 103 | 105 | 105 |
| 4 | 32 | 84.8 | 86.4 | 91 | 95 | 99 | 98 | 103 | 104 | 102 | 109 | 111 | 111 | 116 | 116 | 118 | 116 |
| 5 | 33 | 90.1 | 87.6 | 89 | 93 | 94 | 98 | 106 | 106 | 107 | 112 | 113 | 113 | 117 | 118 | 119 | 118 |
| 5 | 34 | 76.5 | 77.3 | 78 | 79 | 81 | 81 | 83 | 86 | 87 | 90 | 91 | 90 | 92 | 93 | 117 | 99 |
| 5 | 35 | 87.5 | 89.6 | 91 | 95 | 98 | 98 | 105 | 106 | 109 | 114 | 116 | 118 | 122 | 119 | 95 | 120 |
| 5 | 36 | 81 | 82.8 | 84 | 89 | 96 | 93 | 101 | 100 | 101 | 106 | 107 | 107 | 110 | 113 | 122 | 114 |
| 5 | 37 | 74.7 | 74.2 | 83 | 79 | 81 | 85 | 87 | 88 | 91 | 95 | 97 | 98 | 99 | 99 | 100 | 99 |
| 5 | 38 | 79.8 | 81.8 | 81 | 87 | 90 | 90 | 94 | 96 | 98 | 104 | 104 | 105 | 109 | 108 | 112 | 112 |
| 5 | 39 | 77.3 | 76.6 | 75 | 85 | 87 | 88 | 90 | 92 | 94 | 97 | 99 | 99 | 102 | 103 | 106 | 107 |
| 5 | 40 | 80.1 | 78.8 | 80 | 83 | 86 | 86 | 95 | 96 | 97 | 99 | 102 | 100 | 102 | 102 | 104 | 104 |

| Group | Animal | 16 | 17 | 18 | 19 | 20 | 21 | 22 | 23 | 24 | 25 | 26 | 27 | 28 |
|---|---|---|---|---|---|---|---|---|---|---|---|---|---|---|
| 1 | 1 | 109 | 104 | 102 | 109 | 110 | 113 | 113 | 117 | 118 | 119 | 118 | 118 | 116 |
| 1 | 2 | 112 | 106 | 108 | 116 | 115 | 122 | 122 | 127 | 129 | 129 | 128 | 132 | 126 |
| 1 | 3 | 107 | 101 | 99 | 107 | 108 | 111 | 111 | 114 | 116 | 119 | 117 | 118 | 114 |
| 1 | 4 | 105 | 99 | 97 | 105 | 104 | 108 | 125 | 112 | 112 | 114 | 114 | 115 | 111 |
| 1 | 5 | 112 | 106 | 107 | 113 | 113 | 118 | 121 | 121 | 123 | 125 | 124 | 123 | 123 |
| 1 | 6 | 120 | 112 | 111 | 120 | 119 | 127 | 127 | 132 | 134 | 134 | 133 | 134 | 132 |
| 1 | 7 | 105 | 97 | 95 | 105 | 107 | 111 | 113 | 118 | 117 | 121 | 118 | 121 | 120 |
| 1 | 8 | 1131 | 107 | 106 | 111 | 118 | 117 | 117 | 121 | 123 | 125 | 123 | 129 | 123 |
| 2 | 9 | 130 | 122 | 123 | 130 | 124 | 124 | 135 | 142 | 135 | 142 | 137 | 136 | 142 |
| 2 | 10 | 121 | 117 | 110 | 124 | 117 | 117 | 134 | 130 | 124 | 131 | 127 | 125 | 131 |
| 2 | 11 | 104 | 98 | 107 | 105 | 98 | 98 | 100 | 108 | 102 | 108 | 116 | 101 | 107 |
| 2 | 12 | 108 | 101 | 100 | 108 | 102 | 102 | 112 | 120 | 112 | 120 | 104 | 114 | 120 |
| 2 | 13 | 115 | 109 | 108 | 115 | 108 | 107 | 115 | 122 | 116 | 120 | 118 | 114 | 121 |
| 2 | 14 | 105 | 100 | 98 | 109 | 103 | 103 | 110 | 118 | 110 | 117 | 115 | 110 | 117 |
| 2 | 15 | 118 | 111 | 95 | 119 | 111 | 110 | 120 | 128 | 121 | 119 | 118 | 113 | 118 |
| 2 | 16 | 118 | 117 | 114 | 120 | 114 | 114 | 121 | 128 | 126 | 128 | 129 | 124 | 131 |
| 3 | 17 | 107 | 108 | 111 | 111 | 114 | 117 | 110 | 122 | 115 | 126 | 122 | 129 | 127 |
| 3 | 18 | 98 | 100 | 101 | 102 | 105 | 108 | 105 | 110 | 112 | 114 | 111 | 117 | 117 |
| 3 | 19 | 134 | 133 | 138 | 136 | 140 | 141 | 136 | 145 | 147 | 150 | 145 | 153 | 151 |
| 3 | 20 | 113 | 110 | 115 | 112 | 114 | 116 | 112 | 117 | 119 | 121 | 119 | 123 | 120 |
| 3 | 21 | 109 | 106 | 109 | 109 | 110 | 112 | 105 | 114 | 120 | 116 | 114 | 119 | 118 |
| 3 | 22 | 110 | 112 | 114 | 114 | 118 | 118 | 112 | 122 | 124 | 124 | 122 | 129 | 126 |
| 3 | 23 | 119 | 119 | 123 | 123 | 126 | 129 | 120 | 134 | 136 | 137 | 135 | 141 | 139 |
| 3 | 24 | 126 | 128 | 130 | 131 | 133 | 137 | 127 | 140 | 142 | 143 | 142 | 147 | 146 |
| 4 | 25 | 113 | 114 | 116 | 116 | 120 | 119 | 113 | 123 | 126 | 126 | 126 | 129 | 133 |
| 4 | 26 | 126 | 127 | 125 | 130 | 133 | 136 | 136 | 139 | 142 | 142 | 144 | 145 | 147 |
| 4 | 27 | 111 | 114 | 115 | 115 | 118 | 122 | 114 | 126 | 127 | 129 | 130 | 132 | 135 |
| 4 | 28 | 93 | 94 | 96 | 95 | 98 | 99 | 99 | 104 | 103 | 105 | 105 | 107 | 111 |
| 4 | 29 | 110 | 114 | 111 | 115 | 119 | 121 | 112 | 125 | 127 | 129 | 130 | 130 | 134 |

-continued

| | | | | | | | | | | | | | |
|---|---|---|---|---|---|---|---|---|---|---|---|---|---|
| 4 | 30 | 125 | 126 | 120 | 129 | 131 | 133 | 124 | 134 | 135 | 138 | 138 | 138 | 139 |
| 4 | 31 | 112 | 112 | 114 | 115 | 117 | 118 | 112 | 120 | 123 | 127 | 127 | 128 | 131 |
| 4 | 32 | 122 | 123 | 124 | 122 | 124 | 128 | 119 | 130 | 131 | 133 | 131 | 132 | 135 |
| 5 | 33 | 125 | 125 | 128 | 131 | 130 | 136 | 134 | 137 | 135 | 142 | 145 | 148 | 150 |
| 5 | 34 | 103 | 104 | 106 | 106 | 107 | 109 | 113 | 115 | 113 | 120 | 117 | 121 | 123 |
| 5 | 35 | 127 | 127 | 129 | 130 | 130 | 133 | 133 | 137 | 135 | 141 | 141 | 144 | 147 |
| 5 | 36 | 120 | 122 | 125 | 124 | 127 | 132 | 131 | 136 | 135 | 140 | 141 | 144 | 147 |
| 5 | 37 | 105 | 104 | 106 | 107 | 109 | 111 | 110 | 115 | 112 | 118 | 120 | 124 | 126 |
| 5 | 38 | 115 | 118 | 120 | 121 | 121 | 124 | 124 | 129 | 129 | 132 | 133 | 137 | 139 |
| 5 | 39 | 112 | 113 | 115 | 115 | 117 | 120 | 120 | 125 | 127 | 131 | 132 | 133 | 137 |
| 5 | 40 | 108 | 107 | 109 | 111 | 111 | 114 | 113 | 117 | 116 | 121 | 123 | 124 | 125 |

9.2 Appendix 4—Mucositis Scores

| Group | Animal | 6 | 8 | 10 | 12 | 14 | 16 | 18 | 20 | 22 | 24 | 26 | 28 |
|---|---|---|---|---|---|---|---|---|---|---|---|---|---|
| 1 | 1 | 0 | 1 | 2 | 2 | 2 | 3 | 4 | 3 | 2 | 2 | 2 | 2 |
| 1 | 1 | 0 | 1 | 1 | 2 | 2 | 3 | 4 | 3 | 2 | 2 | 2 | 1 |
| 1 | 2 | 0 | 1 | 2 | 3 | 3 | 3 | 3 | 2 | 2 | 1 | 1 | 1 |
| 1 | 2 | 0 | 1 | 1 | 3 | 3 | 3 | 3 | 2 | 2 | 2 | 2 | 1 |
| 1 | 3 | 0 | 1 | 2 | 2 | 3 | 3 | 3 | 3 | 2 | 2 | 2 | 2 |
| 1 | 3 | 0 | 1 | 1 | 2 | 3 | 3 | 3 | 3 | 2 | 2 | 2 | 1 |
| 1 | 4 | 0 | 1 | 2 | 2 | 1 | 1 | 2 | 1 | 1 | 1 | 2 | 2 |
| 1 | 4 | 0 | 1 | 1 | 1 | 2 | 1 | 2 | 2 | 2 | 2 | 2 | 1 |
| 1 | 5 | 0 | 1 | 2 | 2 | 3 | 3 | 3 | 2 | 2 | 2 | 2 | 2 |
| 1 | 5 | 0 | 1 | 1 | 2 | 3 | 3 | 3 | 3 | 2 | 2 | 2 | 1 |
| 1 | 6 | 1 | 1 | 2 | 2 | 3 | 3 | 3 | 2 | 2 | 2 | 2 | 2 |
| 1 | 6 | 1 | 1 | 1 | 2 | 3 | 3 | 3 | 2 | 2 | 2 | 2 | 1 |
| 1 | 7 | 1 | 1 | 2 | 2 | 3 | 3 | 3 | 2 | 2 | 2 | 2 | 2 |
| 1 | 7 | 1 | 1 | 1 | 2 | 3 | 3 | 3 | 2 | 2 | 2 | 2 | 1 |
| 1 | 8 | 1 | 1 | 2 | 3 | 3 | 3 | 3 | 3 | 3 | 2 | 2 | 2 |
| 1 | 8 | 1 | 1 | 1 | 2 | 3 | 3 | 3 | 3 | 3 | 2 | 2 | 2 |
| 2 | 9 | 1 | 1 | 2 | 2 | 2 | 2 | 2 | 2 | 1 | 1 | 1 | 1 |
| 2 | 9 | 1 | 1 | 1 | 2 | 2 | 2 | 2 | 2 | 2 | 2 | 2 | 1 |
| 2 | 10 | 1 | 1 | 2 | 3 | 2 | 2 | 2 | 2 | 2 | 2 | 2 | 2 |
| 2 | 10 | 1 | 1 | 1 | 2 | 2 | 2 | 2 | 2 | 2 | 2 | 2 | 1 |
| 2 | 11 | 1 | 1 | 2 | 2 | 2 | 3 | 3 | 2 | 2 | 1 | 2 |
| 2 | 11 | 1 | 1 | 1 | 2 | 2 | 3 | 3 | 2 | 2 | 2 | 1 |
| 2 | 12 | 0 | 1 | 2 | 2 | 2 | 1 | 2 | 2 | 1 | 2 | 1 |
| 2 | 12 | 0 | 1 | 1 | 2 | 2 | 2 | 2 | 2 | 2 | 2 | 1 |
| 2 | 13 | 0 | 1 | 2 | 2 | 2 | 1 | 1 | 1 | 1 | 2 | 1 |
| 2 | 13 | 0 | 1 | 1 | 1 | 2 | 2 | 2 | 2 | 2 | 2 | 1 |
| 2 | 14 | 0 | 1 | 2 | 2 | 3 | 3 | 3 | 2 | 2 | 2 | 2 |
| 2 | 14 | 0 | 1 | 1 | 1 | 2 | 3 | 3 | 3 | 2 | 2 | 2 | 1 |
| 2 | 15 | 1 | 1 | 2 | 2 | 2 | 2 | 2 | 2 | 2 | 2 | 2 |
| 2 | 15 | 1 | 1 | 1 | 2 | 2 | 2 | 2 | 2 | 2 | 2 | 1 |
| 2 | 16 | 0 | 1 | 2 | 2 | 2 | 2 | 2 | 2 | 2 | 1 | 2 |
| 2 | 16 | 0 | 1 | 1 | 1 | 2 | 2 | 2 | 2 | 2 | 2 | 1 |
| 3 | 17 | 0 | 1 | 2 | 2 | 2 | 3 | 2 | 2 | 1 | 2 | 2 | 1 |
| 3 | 17 | 0 | 1 | 1 | 2 | 2 | 3 | 2 | 2 | 2 | 2 | 2 | 1 |
| 3 | 18 | 1 | 1 | 2 | 2 | 3 | 3 | 3 | 2 | 2 | 2 | 2 | 2 |
| 3 | 18 | 1 | 1 | 1 | 2 | 3 | 3 | 2 | 2 | 2 | 2 | 2 | 1 |
| 3 | 19 | 1 | 1 | 2 | 1 | 2 | 1 | 1 | 1 | 1 | 1 | 1 | 1 |
| 3 | 19 | 1 | 1 | 1 | 2 | 2 | 2 | 2 | 2 | 2 | 2 | 2 | 1 |
| 3 | 20 | 1 | 1 | 2 | 2 | 3 | 3 | 2 | 2 | 2 | 2 | 2 | 2 |
| 3 | 20 | 1 | 1 | 1 | 2 | 3 | 3 | 2 | 2 | 2 | 2 | 2 | 1 |
| 3 | 21 | 1 | 1 | 2 | 2 | 2 | 3 | 2 | 1 | 1 | 2 | 2 | 2 |
| 3 | 21 | 1 | 1 | 1 | 2 | 2 | 2 | 2 | 2 | 2 | 2 | 2 | 1 |
| 3 | 22 | 0 | 1 | 2 | 2 | 2 | 2 | 2 | 2 | 2 | 2 | 1 | 2 |
| 3 | 22 | 0 | 1 | 1 | 2 | 2 | 2 | 2 | 2 | 2 | 2 | 2 | 1 |
| 3 | 23 | 0 | 0 | 2 | 2 | 3 | 2 | 2 | 2 | 2 | 2 | 2 | 2 |
| 3 | 23 | 0 | 0 | 1 | 2 | 3 | 2 | 2 | 2 | 2 | 2 | 2 | 1 |
| 3 | 24 | 0 | 1 | 2 | 2 | 3 | 3 | 2 | 2 | 2 | 2 | 2 | 2 |
| 3 | 24 | 0 | 1 | 1 | 3 | 3 | 3 | 2 | 2 | 2 | 2 | 2 | 1 |
| 4 | 25 | 1 | 1 | 2 | 2 | 3 | 3 | 3 | 3 | 3 | 3 | 3 | 3 |
| 4 | 25 | 1 | 1 | 1 | 2 | 3 | 3 | 3 | 3 | 3 | 3 | 2 | 1 |
| 4 | 26 | 0 | 1 | 2 | 2 | 3 | 3 | 3 | 3 | 3 | 3 | 2 | 2 |
| 4 | 26 | 0 | 1 | 1 | 2 | 3 | 3 | 3 | 3 | 3 | 3 | 2 | 1 |
| 4 | 27 | 1 | 1 | 2 | 2 | 3 | 3 | 3 | 3 | 3 | 3 | 2 | 2 |
| 4 | 27 | 1 | 1 | 1 | 2 | 3 | 3 | 3 | 2 | 2 | 2 | 2 | 1 |
| 4 | 28 | 0 | 1 | 2 | 2 | 3 | 3 | 3 | 2 | 2 | 2 | 2 | 2 |
| 4 | 28 | 0 | 1 | 1 | 2 | 3 | 3 | 3 | 3 | 2 | 2 | 2 | 1 |
| 4 | 29 | 1 | 1 | 2 | 2 | 3 | 3 | 3 | 3 | 2 | 2 | 2 | 2 |
| 4 | 29 | 1 | 1 | 1 | 2 | 3 | 3 | 3 | 2 | 2 | 2 | 2 | 1 |
| 4 | 30 | 0 | 1 | 2 | 2 | 3 | 2 | 2 | 2 | 2 | 2 | 2 | 2 |
| 4 | 30 | 0 | 1 | 1 | 2 | 3 | 2 | 2 | 2 | 2 | 2 | 2 | 1 |
| 4 | 31 | 1 | 1 | 2 | 2 | 3 | 3 | 2 | 2 | 2 | 2 | 2 | 2 |
| 4 | 31 | 1 | 1 | 1 | 2 | 3 | 3 | 2 | 2 | 2 | 2 | 2 | 1 |
| 4 | 32 | 1 | 1 | 2 | 2 | 2 | 2 | 1 | 1 | 1 | 1 | 1 | 2 |
| 4 | 32 | 1 | 1 | 1 | 2 | 2 | 2 | 2 | 2 | 2 | 2 | 2 | 1 |
| 5 | 33 | 1 | 1 | 2 | 2 | 2 | 2 | 2 | 2 | 2 | 2 | 2 | 2 |
| 5 | 33 | 1 | 1 | 1 | 2 | 2 | 2 | 2 | 2 | 2 | 2 | 2 | 1 |
| 5 | 34 | 1 | 1 | 2 | 3 | 2 | 2 | 2 | 2 | 2 | 2 | 2 | 2 |
| 5 | 34 | 1 | 1 | 1 | 2 | 3 | 2 | 2 | 2 | 2 | 2 | 2 | 1 |
| 5 | 35 | 1 | 1 | 2 | 2 | 3 | 3 | 3 | 2 | 2 | 2 | 2 | 2 |
| 5 | 35 | 1 | 1 | 1 | 2 | 3 | 3 | 3 | 2 | 2 | 2 | 2 | 1 |
| 5 | 36 | 0 | 1 | 2 | 2 | 2 | 2 | 2 | 2 | 2 | 2 | 2 | 1 |
| 5 | 36 | 0 | 1 | 1 | 2 | 2 | 2 | 2 | 2 | 2 | 2 | 2 | 1 |
| 5 | 37 | 0 | 1 | 2 | 2 | 3 | 2 | 2 | 2 | 2 | 2 | 2 | 2 |
| 5 | 37 | 0 | 1 | 1 | 2 | 3 | 2 | 2 | 2 | 1 | 2 | 2 | 1 |
| 5 | 38 | 1 | 1 | 2 | 2 | 3 | 2 | 2 | 2 | 2 | 2 | 2 | 2 |
| 5 | 38 | 1 | 1 | 1 | 2 | 3 | 2 | 2 | 2 | 2 | 2 | 2 | 1 |
| 5 | 39 | 1 | 1 | 2 | 2 | 2 | 3 | 3 | 2 | 2 | 2 | 2 | 2 |
| 5 | 39 | 1 | 1 | 1 | 2 | 2 | 3 | 3 | 2 | 2 | 2 | 2 | 1 |
| 5 | 40 | 1 | 1 | 2 | 3 | 3 | 3 | 3 | 2 | 2 | 2 | 2 | 2 |
| 5 | 40 | 1 | 1 | 1 | 3 | 3 | 3 | 3 | 2 | 2 | 2 | 2 | 1 |

Example 3

A Study of the Efficacy of Effect of SCV-07 in the Treatment of Oral Mucositis Induced by Fractionated Radiation in Hamsters 1. Introduction 1.1 Background KGF-1 and other FGF family members have been shown to induce epithelial thickening of the oral and esophageal mucosal surfaces in BDF-1. SCV-07 and the derived SCV-07 peptide are believed to have mechanisms that that may overlap with KGF-1, and have been shown to be protective in other models of mucosal injury.

Oral ulcerative mucositis is a common, painful, dose-limiting toxicity of drug and radiation therapy for cancer. The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of patients receiving antineoplastic drug therapy. The frequency and severity are significantly greater among patients who are treated with induction therapy for leukemia or with many of the conditioning regimens for bone marrow transplant. Among these individuals, moderate to severe mucositis is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through three stages:
1. Painful erythema which can generally be managed by topical anesthetics or non-narcotic analgesics . . . .
2. Painful ulceration often with pseudomembrane formation. In the case of concomitant myelosuppression, bacteremias or sepsis of oral origin are not uncommon. Pain is often of such intensity as to require narcotic analgesia, frequently parenterally.
3. Spontaneous healing, occurring about 2-3 weeks after cessation of anti-neoplastic therapy.

Currently, the only approved biologic or drug for mucositis prevention and/or treatment is Kepivance (palifermin). Kepivance use is limited to mucositis in patients receiving stem cell transplant for hematologic malignancies. Consequently, standard therapy for mucositis consists of palliative rinses, such as saline, bicarbonate solutions, mouthwashes, topical analgesics such as lidocaine and/or systemic administration of narcotics.

The complexity of mucositis as a biological process has only been recently appreciated. It has been suggested that the condition represents a sequential interaction of oral mucosal cells and tissues reactive oxygen species, pro-inflammatory cytokines, mediators of apoptosis, a range of signaling pathways, and local factors such as saliva and the oral micro biota. While epithelial degeneration and breakdown ultimately result in mucosal ulceration, it appears that the early changes associated with radiation-induced mucosal toxicity occur within the endothelium, and connective tissue of the submucosa. It appears that the overall mechanism for mucositis development is similar for both radiation and chemotherapy.

1.2 Fractionated Radiation Model

The fractionated radiation model in hamsters, developed by the Principal Investigator, has proven to be an accurate, efficient and cost-effective technique to provide a preliminary evaluation of anti-mucositis compounds. In this model, hamsters receive 8 doses of 7.5 Gy to the left cheek pouch on days 0, 1, 2, 3, 7, 8, 9 and 10, rather than the single dose of 40 Gy on day 0 that is used in acute radiation studies. The rationale for using this scheduling for the radiation is that it more closely resembles the clinical courses of radiotherapy given to cancer patients. The course of mucositis in this model is well defined and results in peak mucositis scores approximately 14-16 days following radiation. Mortality (generally from the side effects of anesthesia) in the fractionated radiation model is slightly higher than that seen in the acute radiation model and group sizes are increased (to 10 per group) to allow for this.

2. Study Objective and Summary

2.1 Study Objective

The objective of this study was to evaluate the effect of SCV-07, administered by sub-cutaneous injection, on the frequency, severity and duration of oral mucositis induced by a fractionated radiation protocol.

2.2 Study Summary

Forty (40) male Syrian Golden Hamsters were given eight doses of radiation of 7.5 Gy each directed to their left buccal cheek pouch on days 0, 1, 2, 3, 6, 7, 8 and 9. This was accomplished by anesthetizing the animals and everting the left buccal pouch, while protecting the rest of the animal's bodies with a lead shield. Test materials were given by sub-cutaneous injection once daily as detailed in Table 9. Mucositis was evaluated clinically starting on day 7, and continuing on alternate days until day 35. Test articles were given as outlined Table 9, Groups 1 and 2 were dosed from Day −1 to Day 29, Group 3 was dosed on the days of radiation only, Group 4 was dosed on the days between Day −15 and Day 29 on which no radiation is given (Day −1, Day 4, Day 5 and Day 10 to Day 29).

3. Evaluation

3.1 Mucositis Evaluation

The grade of mucositis was scored, beginning day 6, and for every second day thereafter, through and including day 34. The effect on mucositis of each drug treatment compared to placebo was assessed according to the following parameters:
3.1.1 The Difference in the Number of Days Hamsters in Each Group have Ulcerative (Score ≧3) Mucositis.

On each evaluation day, the number of animals with a blinded mucositis score of ≧3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores ≧3) when compared to the control group.

3.1.2 Rank Sum Differences in Daily Mucositis Scores.

For each evaluation day the scores of the control group were compared to those of the treated groups using non-parametric rank sum analysis. Treatment success was considered as a statistically significant lowering of scores in the treated group on 2 or more days from day 6 to day 28.

3.2 Weights and Survival

All animals were weighed daily and their survival recorded, in order to assess possible differences in animal weight among treatment groups as an indication for mucositis severity and/or possible toxicity resulting from the treatments.

4. Study Design

Forty (40) male Syrian Golden Hamsters were given eight doses of radiation of 7.5 Gy each directed to their left buccal cheek pouch on days 0, 1, 2, 3, 6, 7, 8 and 9. This was accomplished by anesthetizing the animals and everting the left buccal pouch, while protecting the rest of the animal's bodies with a lead shield. Test materials were given by sub-cutaneous injection once daily at 8:00 am as detailed in Table 9. Mucositis was evaluated clinically starting on Day 6, and continuing on alternate days until day 34. Test articles were given as outlined Table 9, Groups 1 and 2 was dosed from Day −1 to Day 29, Group 3 was dosed on the days of radiation only (days 0-3 and days 6-10), Group 4 was dosed on the days between Day −1 and Day 29 on which no radiation is given (Day −1, Day 4 to Day 5 and Day 10 to Day 29).

TABLE 9

SCI-03. Study Design

| Group Number | Number of Animals | Treatment | Treatment Schedule | Number of Doses |
|---|---|---|---|---|
| 1 | 10 males | Vehicle Control | Day −1 to Day 29 | 31 |
| 2 | 10 males | SCV-07 100 µg/kg | Day −1 to Day 29 | 31 |
| 3 | 10 males | SCV-07 100 µg/kg | Day 0 to Day 3 and Day 6 to Day 9 | 8 |
| 4 | 10 males | SCV-07 100 µg/kg | Day −1, Days 4, 5 Day 10 to Day 29 | 23 |

Injections of SCV-07 on Days 0, 1, 2, 3, 6, 7, 8 and 9 were given approximately 30 minutes prior to radiation.

5. Material and Methods

5.1 Location of Study Performance

The study was performed at Biomodels AAALAC-accredited facility in Watertown, Mass.

5.2 Animals

Male LVG Syrian Golden Hamsters (Charles River Laboratories), aged 5 to 6 weeks, with average body weight of 81.0 g at study commencement, were used. Animals were individually numbered using an ear punch and housed in small groups of approximately 10 animals per cage. Animals were acclimatized for 5 days prior to study commencement and during this period, the animals were observed daily in order to reject animals that present in poor condition.

5.3 Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained.

5.4 Diet

Animals were fed with a Purina Labdiet® 5061 rodent diet and water was provided ad libitum.

5.5 Animal Randomization and Allocations

Animals were randomly and prospectively divided into four (4) treatment groups prior to irradiation. Each animal was identified by an ear punch corresponding to an individual number. For more consistent identification, ear punch numbering was used rather than tagging, since tags may become dislodged during the course of the study. A cage card was used to identify each cage or label marked with the study number (SCI-03), treatment group number and animal numbers.

5.6 Sub-Cutaneous Dosing and Drug Application

The test compound, human SCV-07 peptide was provided as a powder and dissolved in sterile PBS immediately prior to administration. Drug was given in a volume of 0.1, using a tuberculin syringe with a 27 G needle. Injections were given subcutaneously to the back or abdomen.

5.7 Mucositis Induction

Radiation was generated with a Philips 160 kVp (kilovolt potential) (18.75-ma) X-ray source at a focal distance of 30 cm, with a 3.0 mm hardened Al filtration system. Irradiation was targeted to the left buccal pouch mucosa at a rate of 3.32 Gy/minute. Calibration of this source with a Victoreen model 530 dosimeter indicated that the dose rate was 28.57 nC/min. Using this calibration, the energy received by each animal at each radiation dose was approximately 64.5 nC (nanoCoulombs) at each time point. Prior to irradiation, animals were anesthetized with an intraperitoneal injection of ketamine (160 mg/kg) and xylazine (8 mg/kg). The left buccal pouch was everted, fixed and isolated using a lead shield.

5.8 Mucositis Scoring

The mucositis score, weight change and survival were measured throughout the study as described above. For the evaluation of mucositis, the animals were anesthetized with an inhalation anesthetic, and the left pouch everted. Mucositis was scored visually by comparison to a validated photographic scale, ranging from 0 for normal, to 5 for severe ulceration (clinical scoring). In descriptive terms, this scale is defined as follows:

TABLE 10

SCI-03: Mucositis Scoring.

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas, but no frank ulceration. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |

TABLE 10-continued

SCI-03: Mucositis Scoring.

| Score: | Description: |
|---|---|
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

6. Results 6.1 Survival

One death occurred during this study in the control group on day 8 as a consequence of anesthesia for radiation.

6.2 Weight Change

There were no significant differences in weight changes between study groups. The mean daily percent weight change data was evaluated. The saline treated control hamsters gained an average of 76.3% of their starting weight during the study. Hamsters in the group receiving SCV-07 at 100 µg/kg on days −1 to 29 gained an average of 80.7% of their starting weight during the study. Hamsters in the group receiving SCV-07 at 100 µg/kg on days of radiation only gained an average of 66.3% of their starting weight during the study. Hamsters in the group receiving SCV-07 at 100 µg/kg on day −1, day 4, day 5 and days 10-29 gained an average of 69.7% of their starting weight during the study. The significance of these differences was evaluated by calculating the area-under-the-curve (AUC) for the weight gain of each animal, and then comparing the different treatment groups using a One-Way ANOVA test. The results of this analysis indicated that there were no significant differences between the different treatment groups (P=0.490).

6.3 Mucositis (Tables 11 & 12)

The kinetics and severity of mucositis development among control animals was consistent with that which was expected.

Mean daily mucositis scores for each group were evaluated. In the saline treated control group, the mean peak mucositis score was 3.2, which occurred on day 19. The group receiving SCV-07 from day −1 to day 29 had a peak mean mucositis score of 3.3, which occurred on day 19. The group receiving SCV-07 on the days of radiation (0-3 and 6-9) had a peak mean mucositis score of 3.0, which occurred on day 17. The group receiving SCV-07 on days 1, 4, 5 and 10 through 29 had a peak mean mucositis score of 2.9, which occurred on days 17, 19 and 23. The significance of the differences observed between the different treatment groups was evaluated by calculating the number of days with a score of 3 or higher for each group and comparing these numbers using a chi-squared ($\chi^2$) test. The results of this analysis are shown in Table 11. The hamsters in the saline treated control group had a score of 3 or higher on 36% of the animal days evaluated. In the group receiving SCV-07 from day −1 to day 29, a mucositis score of 3 or higher was observed on 32.7% of the animals days evaluated, which was not statistically significantly different from controls (P=0.448). In the group receiving SCV-07 on days 0-3 and days 6-9, a mucositis score of 3 or higher was observed on 24% of the animals days evaluated, which was statistically significantly different from controls (P=0.002). In the group receiving SCV-07 on days −1, day 4 day 5 and day 10 to day 29, a mucositis score of 3 or higher was observed on 30.7% of the animals days evaluated, which was not statistically significantly different from controls (P=0.204). A further analysis of the mucositis scores was performed using the Mann-Whitney rank sum analysis to compare the scores for each group on each day. The results of this analysis are shown in Table 12. In this analysis, 2 days of significant reduction in the mucositis score are generally required before it is regarded as meaningful. The group treated with SCV-07 on days −1 to 29 was significantly better than the saline controls on days 29 (P=0.004), 31 (P=0.017) and 33 (P=0.002). The group treated with SCV-07 on days 0 to 3 and day 6 to day 9 was significantly better than the saline controls on days 21 (P=0.047), 23 (P<0.001), 25 (P=0.009), 29 (P<0.001), 31 (P=0.015) and 33 (P<0.001). The group treated with SCV-07 on days −1, 4, 5 and days 10 to 29 was significantly better than the saline controls on days 29 (P<0.001), 31 (P=0.004) and 33 (P<0.001).

TABLE 11

SCI-03. Chi-square analysis of the total number of days the animals in each group spent with a score of three or more. This statistic is a measure of severity of ulceration, a clinically important outcome.

| Group | Days >=3 | Days <3 | Total Days | % Days >=3 | Chi Sq v control | P Value |
|---|---|---|---|---|---|---|
| Vehicle (PBS), qd, sc Days −1 to 29 | 98 | 174 | 272 | 36.0 | — | — |
| SCV-07 100 ug/kg, qd, sc Days −1 to 29 | 98 | 202 | 300 | 32.7 | 0.575 | 0.448 |
| SCV-07 100 ug/kg, qd, sc Days 0 to 3 and 6 to 9 | 72 | 228 | 300 | 24.0 | 0.3160 | 0.002 |
| SCV-07 100 ug/kg, qd, sc Days −1, 4, 5 10 to 29 | 92 | 208 | 300 | 30.7 | 0.2300 | 0.204 |

TABLE 12

SCI-03. The significance of group differences observed in daily mucositis scores was determined using the Mann-Whitney rank sum test. This nonparametric statistic is appropriate for the visual mucositis scoring scale. The p values for each calculation are shown. Significant reductions in mucositis scores relative to controls are shown underlined.

| Group Comparison | Day |  |  |  |  |  |  |  |  |  |  |  |  |  |  |
|---|---|---|---|---|---|---|---|---|---|---|---|---|---|---|---|
|  | 7 | 9 | 11 | 13 | 15 | 17 | 19 | 21 | 23 | 25 | 27 | 29 | 31 | 33 | 35 |
| Control vs SCV-7 100 ug/kg, qd, sc Days −1 to 29 | 0.989 | 0.295 | 0.526 | 0.297 | 0.490 | 0.988 | 0.608 | 0.129 | 0.062 | 0.781 | 0.526 | <u>0.004</u> | <u>0.017</u> | <u>0.002</u> | 0.872 |
| Control vs SCV-7 100 ug/kg, qd, sc Days 0 to 3 and 6 to 9 | 0.989 | 0.296 | 0.244 | 0.080 | 0.490 | 0.988 | 0.115 | <u>0.047</u> | <u><0.001</u> | <u>0.009</u> | 0.224 | <u><0.001</u> | <u>0.015</u> | <u><0.001</u> | 0.872 |
| Control vs SCV-7 100 ug/kg, qd, sc Days −1, 4, 5 10 to 29 | 0.989 | 0.605 | 0.918 | 0.406 | 0.164 | 0.605 | 0.115 | 0.129 | 0.648 | 0.420 | 0.528 | <u><0.001</u> | <u>0.004</u> | <u><0.001</u> | 0.490 |

7. Conclusions

1. There was no evidence of any toxicity from SCV-07 in this study based on the observations of mortality and weight gain.
2. Animals treated with human SCV-07 at 100 µg/kg on days on which radiation was administered (days 0-3 and 6-9) showed a statistically significant reduction in the number of days with a mucositis score of 3 or higher (P=0.002), and a significant reduction in mucositis scores on days 21 (P=0.047), 23 (P<0.001), 25 (P=0.009), 29 (P<0.001), 31 (P=0.015) and 33 (P<0.001). This result suggests that SCV-07 may be effective in reducing the overall severity of mucositis, which, consequently, results in enhanced resolution of mucosal injury.
3. Hamsters treated with SCV-07 on days −1 to 29 or on days on which radiation was not administered (days −1, 4, 5 and 10-29), did not show a significant reduction in the number of animal days with a score of 3 or higher, but did show significant reductions in mucositis scores on days 29, 31 and 33.
4. The contrast in effect of SCV-07 based on the schedule of radiation administration may provide some insight into its mechanism of action, but requires further evaluation. The fact that SCV-07 schedules in which the drug was administered on non-radiation days were not as efficacious is of interest, especially for animals treated on consecutive days. Furthermore, the observation that all animals treated with SCV-07 responded identically at the late stages of the study might suggest multiple effects of SCV-07 on the overall pathogenesis and resolution of radiation-induced mucositis.

9. Appendices

9.1 Appendix 5—Animal Weights

| Group | Animal | Day |  |  |  |  |  |  |  |  |  |  |  |  |  |  |  |  |  |
|---|---|---|---|---|---|---|---|---|---|---|---|---|---|---|---|---|---|---|---|
|  |  | −1 | 0 | 1 | 2 | 3 | 4 | 5 | 6 | 7 | 8 | 9 | 10 | 11 | 12 | 13 | 14 | 15 | 16 | 17 |
| 1 | 1 | 82 | 87 | 86 | 88 | 89 | 89 | 94 | 95 | 98 | 97 | 100.8 | 103 | 105 | 108 | 109 | 110 | 110 | 112 | 115 |
| 1 | 2 | 78 | 82 | 81 | 84 | 87 | 85 | 91 | 94 | 95 | Dead |  |  |  |  |  |  |  |  |  |
| 1 | 3 | 79 | 79 | 77 | 76 | 75 | 75 | 77 | 77 | 79 | 80 | 82.2 | 85 | 85 | 89 | 88 | 87 | 86 | 86 | 89 |
| 1 | 4 | 88 | 92 | 93 | 96 | 98 | 99 | 103 | 107 | 108 | 107 | 113.9 | 116 | 116 | 120 | 121 | 123 | 122 | 124 | 125 |
| 1 | 5 | 77 | 80 | 79 | 84 | 88 | 86 | 91 | 93 | 90 | 88 | 96 | 96 | 96 | 97 | 98 | 98 | 98 | 100 | 104 |
| 1 | 6 | 83 | 85 | 90 | 91 | 95 | 94 | 90 | 100 | 100 | 101 | 106.1 | 107 | 109 | 112 | 113 | 114 | 115 | 115 | 118 |
| 1 | 7 | 76 | 78 | 78 | 79 | 81 | 83 | 98 | 88 | 90 | 89 | 93.4 | 95 | 93 | 96 | 98 | 98 | 99 | 99 | 102 |
| 1 | 8 | 73 | 76 | 75 | 76 | 77 | 78 | 84 | 86 | 86 | 87 | 90.5 | 93 | 97 | 98 | 99 | 101 | 103 | 102 | 103 |
| 1 | 9 | 81 | 86 | 87 | 88 | 87 | 90 | 94 | 99 | 98 | 100 | 104.4 | 105 | 108 | 111 | 113 | 113 | 114 | 114 | 119 |
| 1 | 10 | 79 | 83 | 84 | 82 | 84 | 80 | 88 | 90 | 91 | 90 | 93.7 | 95 | 95 | 97 | 96 | 97 | 95 | 100 | 102 |
| 2 | 11 | 82 | 86 | 89 | 78 | 77 | 80 | 83 | 88 | 88 | 89 | 94.5 | 95 | 98 | 100 | 103 | 104 | 104 | 105 | 108 |
| 2 | 12 | 80 | 82 | 82 | 83 | 86 | 85 | 88 | 92 | 91 | 90 | 93.4 | 92 | 95 | 96 | 97 | 96 | 97 | 99 | 100 |
| 2 | 13 | 82 | 84 | 84 | 87 | 88 | 88 | 92 | 94 | 93 | 94 | 98.3 | 100 | 99 | 103 | 104 | 106 | 105 | 107 | 108 |
| 2 | 14 | 73 | 77 | 76 | 79 | 79 | 82 | 84 | 87 | 87 | 87 | 90.6 | 92 | 96 | 97 | 97 | 98 | 99 | 99 | 101 |
| 2 | 15 | 82 | 87 | 89 | 92 | 95 | 95 | 98 | 102 | 102 | 103 | 108.5 | 108 | 110 | 114 | 115 | 116 | 117 | 117 | 120 |
| 2 | 16 | 83 | 85 | 88 | 91 | 94 | 93 | 97 | 102 | 99 | 99 | 103.5 | 105 | 107 | 111 | 111 | 109 | 108 | 109 | 111 |
| 2 | 17 | 81 | 82 | 83 | 87 | 88 | 87 | 91 | 95 | 93 | 95 | 99.7 | 97 | 101 | 104 | 106 | 105 | 107 | 106 | 107 |
| 2 | 18 | 76 | 77 | 76 | 80 | 79 | 79 | 84 | 86 | 85 | 87 | 88.2 | 92 | 92 | 95 | 94 | 95 | 94 | 96 | 97 |
| 2 | 19 | 84 | 87 | 87 | 88 | 90 | 91 | 94 | 98 | 100 | 98 | 102.3 | 104 | 104 | 107 | 108 | 108 | 108 | 111 | 110 |
| 2 | 20 | 69 | 70 | 74 | 76 | 75 | 76 | 79 | 79 | 84 | 84 | 88.6 | 90 | 94 | 97 | 98 | 98 | 98 | 99 | 103 |
| 3 | 21 | 87 | 92 | 92 | 97 | 94 | 95 | 100 | 104 | 106 | 103 | 110.6 | 111 | 112 | 102 | 114 | 113 | 112 | 113 | 118 |
| 3 | 22 | 76 | 78 | 79 | 80 | 80 | 82 | 85 | 89 | 90 | 88 | 94.6 | 95 | 96 | 110 | 101 | 100 | 100 | 103 | 106 |
| 3 | 23 | 93 | 98 | 95 | 102 | 104 | 102 | 108 | 111 | 115 | 113 | 117.4 | 119 | 122 | 125 | 124 | 125 | 126 | 129 | 132 |
| 3 | 24 | 78 | 82 | 79 | 80 | 82 | 81 | 85 | 88 | 89 | 88 | 92.6 | 93 | 95 | 97 | 98 | 99 | 97 | 97 | 100 |
| 3 | 25 | 80 | 84 | 82 | 85 | 84 | 86 | 88 | 90 | 91 | 93 | 94.4 | 96 | 99 | 101 | 103 | 100 | 102 | 101 | 104 |
| 3 | 26 | 87 | 89 | 86 | 88 | 86 | 86 | 89 | 91 | 89 | 90 | 93.7 | 95 | 97 | 98 | 101 | 100 | 101 | 100 | 101 |
| 3 | 27 | 84 | 87 | 87 | 88 | 89 | 88 | 93 | 97 | 97 | 97 | 101.7 | 103 | 104 | 103 | 109 | 112 | 111 | 113 | 115 |
| 3 | 28 | 80 | 82 | 83 | 84 | 88 | 85 | 88 | 94 | 93 | 94 | 97.5 | 98 | 99 | 99 | 105 | 103 | 105 | 106 | 106 |

-continued

| | | | | | | | | | | | | | | | | | | | | |
|---|---|---|---|---|---|---|---|---|---|---|---|---|---|---|---|---|---|---|---|---|
| 3 | 29 | 79 | 79 | 78 | 81 | 83 | 83 | 87 | 89 | 90 | 88 | 91.6 | 94 | 94 | 96 | 96 | 97 | 96 | 99 | 102 |
| 3 | 30 | 76 | 76 | 73 | 74 | 76 | 74 | 77 | 78 | 78 | 78 | 79.2 | 80 | 81 | 84 | 84 | 84 | 82 | 85 | 86 |
| 4 | 31 | 80 | 84 | 85 | 89 | 90 | 93 | 94 | 96 | 97 | 98 | 101.2 | 102 | 104 | 105 | 107 | 105 | 106 | 109 | 111 |
| 4 | 32 | 85 | 88 | 90 | 91 | 94 | 94 | 99 | 102 | 103 | 105 | 110.3 | 110 | 112 | 116 | 116 | 116 | 116 | 117 | 117 |
| 4 | 33 | 82 | 85 | 82 | 96 | 87 | 85 | 89 | 92 | 93 | 91 | 95.3 | 95 | 96 | 97 | 97 | 96 | 96 | 96 | 96 |
| 4 | 34 | 87 | 89 | 87 | 90 | 86 | 91 | 97 | 99 | 101 | 103 | 108.6 | 110 | 110 | 115 | 117 | 118 | 120 | 122 | 123 |
| 4 | 35 | 84 | 89 | 90 | 92 | 97 | 97 | 104 | 107 | 110 | 108 | 111.7 | 114 | 115 | 117 | 119 | 121 | 122 | 124 | 127 |
| 4 | 36 | 85 | 90 | 89 | 91 | 94 | 96 | 98 | 101 | 103 | 102 | 104.7 | 108 | 107 | 109 | 110 | 110 | 111 | 112 | 113 |
| 4 | 37 | 87 | 91 | 91 | 92 | 94 | 95 | 98 | 101 | 102 | 102 | 106.7 | 108 | 109 | 112 | 113 | 113 | 113 | 113 | 114 |
| 4 | 38 | 89 | 94 | 92 | 97 | 98 | 99 | 106 | 106 | 109 | 106 | 110.6 | 112 | 114 | 115 | 117 | 117 | 119 | 121 | 122 |
| 4 | 39 | 70 | 73 | 72 | 73 | 73 | 73 | 76 | 79 | 78 | 79 | 80.7 | 80 | 78 | 82 | 81 | 83 | 83 | 86 | 87 |
| 4 | 40 | 81 | 87 | 86 | 85 | 88 | 87 | 87 | 90 | 92 | 89 | 90.6 | 89 | 90 | 93 | 88 | 88 | 89 | 94 | 97 |

| Group | Animal | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|
| 1 | 1 | 115 | 117 | 119 | 120 | 122 | 124 | 125 | 126 | 130 | 130 | 132 | 132 | 135 | 137 | 137 | 141 | 143 | 144 |
| 1 | 2 | | | | | | | | | | | | | | | | | | |
| 1 | 3 | 90 | 95 | 95 | 97 | 98 | 101 | 101 | 102 | 106 | 108 | 107 | 108 | 111 | 114 | 115 | 119 | 118 | 120 |
| 1 | 4 | 126 | 129 | 130 | 128 | 130 | 133 | 131 | 131 | 134 | 135 | 138 | 136 | 138 | 138 | 139 | 143 | 142 | 143 |
| 1 | 5 | 105 | 106 | 109 | 113 | 114 | 117 | 120 | 121 | 126 | 129 | 129 | 128 | 134 | 135 | 137 | 142 | 143 | 142 |
| 1 | 6 | 120 | 123 | 126 | 128 | 130 | 132 | 138 | 138 | 144 | 147 | 146 | 147 | 152 | 155 | 155 | 160 | 159 | 159 |
| 1 | 7 | 103 | 109 | 111 | 111 | 111 | 116 | 118 | 118 | 124 | 123 | 125 | 125 | 130 | 131 | 133 | 137 | 138 | 137 |
| 1 | 8 | 103 | 110 | 109 | 110 | 112 | 115 | 115 | 117 | 121 | 122 | 123 | 121 | 126 | 129 | 129 | 133 | 131 | 134 |
| 1 | 9 | 120 | 124 | 128 | 126 | 129 | 132 | 132 | 134 | 138 | 139 | 140 | 140 | 145 | 146 | 147 | 151 | 155 | 153 |
| 1 | 10 | 105 | 105 | 109 | 110 | 113 | 114 | 115 | 118 | 121 | 120 | 122 | 124 | 125 | 129 | 131 | 133 | | |
| 2 | 11 | 108 | 113 | 114 | 116 | 117 | 120 | 122 | 123 | 129 | 131 | 134 | 132 | 136 | 138 | 141 | 146 | 145 | 146 |
| 2 | 12 | 98 | 104 | 105 | 107 | 108 | 111 | 113 | 113 | 117 | 116 | 118 | 118 | 122 | 124 | 126 | 131 | 130 | 131 |
| 2 | 13 | 109 | 114 | 116 | 117 | 119 | 120 | 124 | 124 | 129 | 130 | 130 | 130 | 137 | 138 | 141 | 136 | 145 | 136 |
| 2 | 14 | 103 | 107 | 109 | 110 | 112 | 114 | 116 | 117 | 121 | 124 | 124 | 123 | 128 | 131 | 120 | 145 | 136 | 145 |
| 2 | 15 | 120 | 124 | 126 | 127 | 127 | 130 | 132 | 132 | 137 | 138 | 139 | 139 | 142 | 143 | 143 | 147 | 146 | 147 |
| 2 | 16 | 113 | 116 | 117 | 122 | 123 | 126 | 128 | 128 | 132 | 133 | 135 | 134 | 138 | 142 | 142 | 148 | 147 | 148 |
| 2 | 17 | 118 | 122 | 121 | 126 | 127 | 130 | 130 | 132 | 136 | 137 | 140 | 140 | 144 | 146 | 147 | 152 | 153 | 154 |
| 2 | 18 | 98 | 102 | 103 | 104 | 105 | 108 | 111 | 110 | 114 | 115 | 114 | 120 | 121 | 122 | 125 | 125 | 127 | |
| 2 | 19 | 113 | 115 | 116 | 119 | 120 | 120 | 123 | 126 | 129 | 130 | 133 | 133 | 137 | 139 | 139 | 144 | 147 | 146 |
| 2 | 20 | 106 | 108 | 111 | 118 | 117 | 118 | 120 | 121 | 124 | 126 | 131 | 127 | 133 | 138 | 138 | 144 | 146 | 147 |
| 3 | 21 | 117 | 122 | 123 | 124 | 127 | 127 | 128 | 128 | 131 | 133 | 134 | 132 | 135 | 138 | 139 | 143 | 143 | 144 |
| 3 | 22 | 109 | 112 | 114 | 115 | 114 | 121 | 122 | 121 | 124 | 125 | 127 | 126 | 130 | 132 | 133 | 136 | 136 | 137 |
| 3 | 23 | 137 | 138 | 141 | 141 | 144 | 152 | 148 | 150 | 153 | 158 | 158 | 158 | 162 | 165 | 165 | 172 | 171 | 170 |
| 3 | 24 | 101 | 105 | 107 | 108 | 108 | 113 | 114 | 115 | 119 | 119 | 122 | 122 | 126 | 128 | 128 | 133 | 134 | 135 |
| 3 | 25 | 104 | 108 | 109 | 108 | 112 | 113 | 115 | 116 | 117 | 119 | 121 | 120 | 122 | 123 | 124 | 127 | 127 | 128 |
| 3 | 26 | 102 | 106 | 108 | 109 | 111 | 113 | 115 | 116 | 122 | 119 | 121 | 122 | 125 | 128 | 130 | 133 | 133 | 135 |
| 3 | 27 | 108 | 111 | 112 | 114 | 115 | 118 | 120 | 121 | 124 | 124 | 125 | 126 | 129 | 131 | 131 | 132 | 134 | 134 |
| 3 | 28 | 108 | 113 | 114 | 114 | 118 | 120 | 121 | 122 | 120 | 126 | 128 | 128 | 132 | 134 | 134 | 140 | 138 | 140 |
| 3 | 29 | 104 | 107 | 107 | 109 | 111 | 114 | 115 | 114 | 119 | 222 | 120 | 121 | 125 | 125 | 128 | 131 | 131 | 132 |
| 3 | 30 | 87 | 90 | 90 | 93 | 93 | 96 | 95 | 95 | 97 | 97 | 100 | 99 | 102 | 104 | 103 | 107 | 107 | 110 |
| 4 | 31 | 112 | 118 | 118 | 120 | 124 | 124 | 123 | 125 | 126 | 129 | 131 | 131 | 133 | 136 | 138 | 141 | 140 | 141 |
| 4 | 32 | 114 | 120 | 121 | 124 | 124 | 127 | 128 | 131 | 134 | 134 | 136 | 134 | 138 | 142 | 142 | 146 | 147 | 146 |
| 4 | 33 | 95 | 98 | 99 | 101 | 102 | 105 | 107 | 108 | 110 | 114 | 114 | 112 | 116 | 118 | 119 | 122 | 122 | 124 |
| 4 | 34 | 122 | 128 | 128 | 131 | 133 | 135 | 138 | 139 | 142 | 143 | 145 | 146 | 150 | 152 | 153 | 158 | 157 | 158 |
| 4 | 35 | 127 | 132 | 133 | 136 | 134 | 137 | 138 | 140 | 143 | 144 | 146 | 144 | 149 | 151 | 152 | 157 | 158 | 159 |
| 4 | 36 | 115 | 119 | 118 | 120 | 122 | 123 | 124 | 128 | 128 | 131 | 131 | 131 | 136 | 136 | 138 | 141 | 140 | 141 |
| 4 | 37 | 113 | 118 | 118 | 119 | 120 | 120 | 123 | 122 | 123 | 127 | 128 | 128 | 132 | 134 | 134 | 137 | 139 | 140 |
| 4 | 38 | 121 | 127 | 128 | 131 | 133 | 135 | 135 | 137 | 139 | 140 | 142 | 142 | 146 | 150 | 149 | 154 | 153 | 154 |
| 4 | 39 | 88 | 92 | 92 | 94 | 95 | 97 | 99 | 98 | 100 | 102 | 103 | 102 | 105 | 108 | 109 | 112 | 112 | 113 |
| 4 | 40 | 98 | 102 | 104 | 109 | 109 | 111 | 112 | 113 | 118 | 121 | 122 | 118 | 126 | 126 | 129 | 132 | 133 | 134 |

9.2 Appendix 6—Mucositis Scores

| | | Day Number | | | | | | | | | | | | | | |
|---|---|---|---|---|---|---|---|---|---|---|---|---|---|---|---|---|
| Group | Animal | 7 | 9 | 11 | 13 | 15 | 17 | 19 | 21 | 23 | 25 | 27 | 29 | 31 | 33 | 35 |
| 1 | 1 | 0 | 1 | 1 | 1 | 2 | 3 | 4 | 3 | 3 | 3 | 3 | 2 | 2 | 2 | 1 |
| 1 | 1 | 0 | 1 | 1 | 1 | 2 | 3 | 4 | 3 | 3 | 3 | 3 | 2 | 2 | 2 | 1 |
| 1 | 2 | 0 | dead | | | | | | | | | | | | | |
| 1 | 2 | 0 | | | | | | | | | | | | | | |
| 1 | 3 | 0 | 1 | 1 | 2 | 3 | 3 | 4 | 3 | 3 | 2 | 2 | 2 | 2 | 2 | 1 |
| 1 | 3 | 0 | 1 | 1 | 2 | 3 | 3 | 4 | 3 | 3 | 2 | 2 | 2 | 2 | 2 | 1 |
| 1 | 4 | 0 | 1 | 1 | 2 | 3 | 3 | 3 | 3 | 3 | 2 | 2 | 1 | 1 | 2 | 1 |
| 1 | 4 | 0 | 1 | 1 | 2 | 3 | 3 | 3 | 3 | 3 | 2 | 2 | 1 | 1 | 2 | 1 |
| 1 | 5 | 0 | 1 | 2 | 2 | 3 | 3 | 3 | 2 | 2 | 2 | 2 | 2 | 2 | 2 | 1 |
| 1 | 5 | 0 | 1 | 2 | 2 | 3 | 3 | 3 | 2 | 2 | 2 | 2 | 2 | 2 | 2 | 1 |
| 1 | 6 | 0 | 1 | 1 | 2 | 3 | 3 | 3 | 3 | 3 | 3 | 2 | 2 | 2 | 2 | 1 |
| 1 | 6 | 0 | 1 | 1 | 2 | 3 | 3 | 3 | 3 | 3 | 3 | 2 | 2 | 2 | 2 | 1 |

-continued

| | | Day Number | | | | | | | | | | | | | |
|---|---|---|---|---|---|---|---|---|---|---|---|---|---|---|---|
| Group | Animal | 7 | 9 | 11 | 13 | 15 | 17 | 19 | 21 | 23 | 25 | 27 | 29 | 31 | 33 | 35 |
| 1 | 7 | 0 | 1 | 1 | 2 | 3 | 3 | 3 | 3 | 3 | 2 | 2 | 1 | 1 | 1 | 0 |
| 1 | 7 | 0 | 1 | 1 | 2 | 3 | 3 | 3 | 3 | 3 | 2 | 2 | 1 | 1 | 1 | 0 |
| 1 | 8 | 0 | 1 | 1 | 1 | 2 | 3 | 3 | 4 | 4 | 3 | 2 | 2 | 1 | 1 | 0 |
| 1 | 8 | 0 | 1 | 1 | 1 | 2 | 3 | 3 | 4 | 4 | 3 | 2 | 2 | 1 | 1 | 0 |
| 1 | 9 | 0 | 1 | 1 | 1 | 2 | 3 | 3 | 3 | 3 | 2 | 2 | 1 | 0 | 1 | 0 |
| 1 | 9 | 0 | 1 | 1 | 1 | 2 | 3 | 3 | 3 | 3 | 2 | 2 | 1 | 0 | 1 | 0 |
| 1 | 10 | 0 | 1 | 2 | 2 | 3 | 3 | 3 | 3 | 3 | 3 | 3 | 3 | 3 | 2 | 1 |
| 1 | 10 | 0 | 1 | 2 | 2 | 3 | 3 | 3 | 3 | 3 | 3 | 3 | 3 | 3 | 2 | 1 |
| 2 | 11 | 0 | 1 | 1 | 2 | 3 | 3 | 3 | 3 | 3 | 3 | 3 | 2 | 2 | 1 | |
| 2 | 11 | 0 | 1 | 1 | 2 | 3 | 3 | 3 | 3 | 3 | 3 | 3 | 2 | 2 | 1 | |
| 2 | 12 | 0 | 0 | 1 | 3 | 3 | 3 | 3 | 3 | 3 | 2 | 2 | 1 | 0 | 1 | 0 |
| 2 | 12 | 0 | 0 | 1 | 3 | 3 | 3 | 3 | 3 | 3 | 2 | 2 | 1 | 0 | 1 | 0 |
| 2 | 13 | 0 | 1 | 1 | 2 | 3 | 3 | 4 | 3 | 2 | 2 | 2 | 1 | 1 | 1 | 0 |
| 2 | 13 | 0 | 1 | 1 | 2 | 3 | 3 | 4 | 3 | 2 | 2 | 2 | 1 | 1 | 1 | 0 |
| 2 | 14 | 0 | 1 | 1 | 2 | 3 | 3 | 4 | 3 | 3 | 3 | 2 | 1 | 1 | 1 | 1 |
| 2 | 14 | 0 | 1 | 1 | 2 | 3 | 3 | 4 | 3 | 3 | 3 | 2 | 1 | 1 | 1 | 1 |
| 2 | 15 | 0 | 1 | 1 | 2 | 2 | 3 | 3 | 3 | 2 | 3 | 2 | 1 | 1 | 1 | 1 |
| 2 | 15 | 0 | 1 | 1 | 2 | 3 | 3 | 3 | 3 | 2 | 3 | 2 | 1 | 1 | 1 | 1 |
| 2 | 16 | 0 | 1 | 1 | 2 | 3 | 3 | 4 | 3 | 3 | 3 | 2 | 1 | 1 | 1 | 1 |
| 2 | 16 | 0 | 1 | 1 | 2 | 3 | 3 | 4 | 3 | 3 | 3 | 2 | 1 | 1 | 1 | 1 |
| 2 | 17 | 0 | 1 | 1 | 1 | 3 | 3 | 2 | 2 | 3 | 2 | 2 | 1 | 0 | 0 | 0 |
| 2 | 17 | 0 | 1 | 1 | 1 | 3 | 3 | 2 | 2 | 3 | 2 | 2 | 1 | 0 | 0 | 0 |
| 2 | 18 | 0 | 1 | 1 | 1 | 2 | 3 | 3 | 3 | 2 | 3 | 2 | 0 | 1 | 1 | 1 |
| 2 | 18 | 0 | 1 | 1 | 1 | 2 | 3 | 3 | 3 | 2 | 3 | 2 | 0 | 1 | 1 | 1 |
| 2 | 19 | 0 | 0 | 2 | 2 | 3 | 3 | 3 | 3 | 3 | 2 | 2 | 1 | 1 | 1 | 1 |
| 2 | 19 | 0 | 0 | 2 | 2 | 3 | 3 | 3 | 3 | 3 | 2 | 2 | 1 | 1 | 1 | 1 |
| 2 | 20 | 0 | 1 | 1 | 2 | 3 | 3 | 4 | 2 | 2 | 2 | 2 | 1 | 1 | 1 | 1 |
| 2 | 20 | 0 | 1 | 1 | 2 | 3 | 3 | 4 | 2 | 2 | 2 | 2 | 1 | 1 | 1 | 1 |
| 3 | 21 | 0 | 1 | 1 | 2 | 3 | 3 | 3 | 3 | 2 | 2 | 2 | 1 | 2 | 1 | 1 |
| 3 | 21 | 0 | 1 | 1 | 2 | 3 | 3 | 3 | 3 | 2 | 2 | 2 | 1 | 2 | 1 | 1 |
| 3 | 22 | 0 | 2 | 1 | 2 | 3 | 3 | 3 | 2 | 2 | 2 | 2 | 0 | 0 | 0 | 0 |
| 3 | 22 | 0 | 2 | 1 | 2 | 3 | 3 | 3 | 2 | 2 | 2 | 2 | 0 | 0 | 0 | 0 |
| 3 | 23 | 0 | 0 | 1 | 2 | 3 | 3 | 3 | 2 | 2 | 2 | 2 | 1 | 0 | 1 | 1 |
| 3 | 23 | 0 | 0 | 1 | 2 | 3 | 3 | 3 | 2 | 2 | 2 | 2 | 1 | 0 | 1 | 1 |
| 3 | 24 | 0 | 1 | 1 | 2 | 3 | 3 | 3 | 3 | 2 | 2 | 2 | 1 | 1 | 1 | 1 |
| 3 | 24 | 0 | 1 | 1 | 2 | 3 | 3 | 3 | 3 | 2 | 2 | 2 | 1 | 1 | 1 | 1 |
| 3 | 25 | 0 | 1 | 1 | 2 | 3 | 3 | 3 | 3 | 2 | 2 | 2 | 1 | 1 | 1 | 1 |
| 3 | 25 | 0 | 1 | 1 | 2 | 3 | 3 | 3 | 3 | 2 | 2 | 2 | 1 | 1 | 1 | 1 |
| 3 | 26 | 0 | 0 | 1 | 2 | 2 | 3 | 3 | 3 | 2 | 2 | 2 | 1 | 1 | 1 | 1 |
| 3 | 26 | 0 | 0 | 1 | 2 | 2 | 3 | 3 | 3 | 2 | 2 | 2 | 1 | 1 | 1 | 1 |
| 3 | 27 | 0 | 1 | 1 | 2 | 3 | 3 | 3 | 3 | 3 | 2 | 2 | 1 | 1 | 1 | 1 |
| 3 | 27 | 0 | 1 | 1 | 2 | 3 | 3 | 3 | 3 | 3 | 2 | 2 | 1 | 1 | 1 | 1 |
| 3 | 28 | 0 | 1 | 1 | 2 | 3 | 3 | 3 | 3 | 3 | 2 | 2 | 1 | 0 | 1 | 0 |
| 3 | 28 | 0 | 1 | 1 | 2 | 3 | 3 | 3 | 3 | 3 | 2 | 2 | 1 | 0 | 1 | 0 |
| 3 | 29 | 0 | 0 | 1 | 2 | 3 | 3 | 3 | 3 | 2 | 2 | 2 | 1 | 2 | 1 | 1 |
| 3 | 29 | 0 | 0 | 1 | 2 | 3 | 3 | 3 | 3 | 2 | 2 | 2 | 1 | 2 | 1 | 1 |
| 3 | 30 | 0 | 1 | 1 | 2 | 2 | 3 | 2 | 2 | 2 | 1 | 2 | 0 | 0 | 0 | 0 |
| 3 | 30 | 0 | 1 | 1 | 2 | 2 | 3 | 2 | 2 | 2 | 1 | 2 | 0 | 0 | 0 | 0 |
| 4 | 31 | 0 | 0 | 1 | 2 | 3 | 3 | 3 | 3 | 3 | 2 | 2 | 1 | 0 | 1 | 0 |
| 4 | 31 | 0 | 0 | 1 | 2 | 3 | 3 | 3 | 3 | 3 | 2 | 2 | 1 | 0 | 1 | 0 |
| 4 | 32 | 0 | 1 | 1 | 2 | 2 | 3 | 3 | 2 | 2 | 3 | 2 | 0 | 1 | 1 | 1 |
| 4 | 32 | 0 | 1 | 1 | 2 | 2 | 3 | 3 | 2 | 2 | 3 | 2 | 0 | 1 | 1 | 1 |
| 4 | 33 | 0 | 1 | 1 | 2 | 2 | 3 | 3 | 3 | 3 | 2 | 2 | 0 | 1 | 1 | 1 |
| 4 | 33 | 0 | 1 | 1 | 2 | 2 | 3 | 3 | 3 | 3 | 2 | 2 | 0 | 1 | 1 | 1 |
| 4 | 34 | 0 | 1 | 1 | 1 | 2 | 2 | 3 | 3 | 3 | 3 | 2 | 2 | 2 | 2 | 1 |
| 4 | 34 | 0 | 1 | 1 | 1 | 2 | 2 | 3 | 3 | 3 | 3 | 2 | 2 | 2 | 2 | 1 |
| 4 | 35 | 0 | 1 | 2 | 2 | 3 | 3 | 3 | 3 | 3 | 2 | 1 | 0 | 1 | 1 | |
| 4 | 35 | 0 | 1 | 2 | 2 | 3 | 3 | 3 | 3 | 3 | 2 | 1 | 0 | 1 | 1 | |
| 4 | 36 | 0 | 1 | 1 | 2 | 2 | 3 | 3 | 3 | 3 | 2 | 1 | 1 | 1 | 1 | 1 |
| 4 | 36 | 0 | 1 | 1 | 2 | 2 | 3 | 3 | 3 | 3 | 2 | 1 | 1 | 1 | 1 | 1 |
| 4 | 37 | 0 | 1 | 1 | 1 | 2 | 3 | 3 | 3 | 3 | 3 | 2 | 0 | 1 | 1 | 1 |
| 4 | 37 | 0 | 1 | 1 | 1 | 2 | 3 | 3 | 3 | 3 | 3 | 2 | 0 | 1 | 1 | 1 |
| 4 | 38 | 0 | 1 | 1 | 2 | 2 | 3 | 3 | 3 | 3 | 3 | 3 | 1 | 1 | 1 | 1 |
| 4 | 38 | 0 | 1 | 1 | 2 | 2 | 3 | 3 | 3 | 3 | 3 | 3 | 1 | 1 | 1 | 1 |
| 4 | 39 | 0 | 1 | 1 | 2 | 3 | 3 | 3 | 3 | 2 | 2 | 1 | 0 | 0 | 0 | |
| 4 | 39 | 0 | 1 | 1 | 2 | 3 | 3 | 3 | 3 | 2 | 2 | 1 | 0 | 0 | 0 | |
| 4 | 40 | 0 | 1 | 2 | 2 | 3 | 3 | 2 | 2 | 3 | 2 | 2 | 1 | 0 | 0 | 0 |
| 4 | 40 | 0 | 1 | 2 | 2 | 3 | 3 | 2 | 2 | 3 | 2 | 2 | 1 | 0 | 0 | 0 |

Example 4

A Study of SCV-07 in the Treatment of Oral Mucositis Induced by a Combination of Cisplatin and Acute Radiation in Hamsters Introduction Prior studies with SCV-07 have shown that it is effective in treating oral mucositis in hamster models of the disease induced by both acute and fractionated radiation. In this study, the efficacy of SCV-07 was evaluated in a hamster model of oral mucositis induced by a combination of chemotherapy and radiation, and specifically, by the combination of cis-platin and radiation.

Methods

Forty Golden Syrian hamsters were prospectively randomized into four equally sized groups. Mucositis was induced on the left cheek pouch mucosa of golden Syrian hamsters by a single dose of cis-platin at 5 mg/kg given on day −1, and a single dose of radiation administered on day 0 at a dose of 35Gy. Beginning on day −1 and continuing once daily until day 20, SCV-07 was given by sub-cutaneous injection at doses of 10 µg/kg, 100 µg/kg or 1 mg/kg in a volume of 100 µL. Animals' activity and weight were evaluated daily. Beginning on day 6 and continuing on alternate days for the duration of the study, oral mucositis was evaluated using a standard scoring six point scale. The number of days of ulcerative mucositis was evaluated using a Chi-squared test of scores of ≧3 throughout the study, and the individual daily group scores were assessed with a Rank Sum Test.

Results

Mucositis was favorably and consistently impacted in animals treated with SCV-07 in all test groups. Severe mucositis was reduced from 50% of animals days evaluated in vehicle controls to approximately 30% in SCV-07 treated animals. The most significant impact was seen in the later stages of the disease process, after the peak of mucositis. No significant differences were observed among groups relative to weight changes. No animals died during the course of the experiment.

Conclusions

1. There was no evidence of any toxicity from SCV-07 in this study based on the observations of mortality and weight gain.
2. Animals treated with SCV-07 at 10 µg/kg from day −1 to day 20 showed a statistically significant reduction in the number of days with a mucositis score of 3 or higher ($P<0.001$), and a significant reduction in mucositis scores on days 22 ($P=0.010$), 24 ($P=0.022$), 26 ($P=0.015$), and 28 ($P<0.001$).
3. Animals treated with SCV-07 at 100 µg/kg from day −1 to day 20 showed a statistically significant reduction in the number of days with a mucositis score of 3 or higher ($P<0.001$), and a significant reduction in mucositis scores on days 6 ($P=0.015$), 22 ($P=0.003$), 24 ($P=0.005$), 26 ($P<0.001$), and 28 ($P<0.001$).
4. Animals treated with SCV-07 at 1 mg/kg from day −1 to day 20 showed a statistically significant reduction in the number of days with a mucositis score of 3 or higher ($P<0.001$), and a significant reduction in mucositis scores on days 6 ($P=0.015$), 20 ($P=0.029$), 22 ($P=0.012$), 24 ($P=0.001$), 26 ($P=0.003$), and 28 ($P<0.001$).

1.1 Background

KGF-1 and other FGF family members have been shown to induce epithelial thickening of the oral and esophageal mucosal surfaces in BDF-1. SCV-07 and the derived SCV-07 peptide are believed to have mechanisms that that may overlap with KGF-1, and have been shown to be protective in other models of mucosal injury.

Oral ulcerative mucositis is a common, painful, dose-limiting toxicity of drug and radiation therapy for cancer. The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia. Mucositis occurs to some degree in more than one third of patients receiving anti-neoplastic drug therapy. The frequency and severity are significantly greater among patients who are treated with induction therapy for leukemia or with many of the conditioning regimens for bone marrow transplant. Among these individuals, moderate to severe mucositis is not unusual in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached.

Clinically mucositis progresses through three stages:
1. Painful erythema which can generally be managed by topical anesthetics or non-narcotic analgesics.
2. Painful ulceration often with pseudomembrane formation. In the case of concomitant myelosuppression, bacteremias or sepsis of oral origin are not uncommon. Pain is often of such intensity as to require narcotic analgesia, frequently parenterally.
3. Spontaneous healing, occurring about 2-3 weeks after cessation of anti-neoplastic therapy.

Currently, the only approved biologic or drug for mucositis prevention and/or treatment is Kepivance (palifermin). Kepivance use is limited to mucositis in patients receiving stem cell transplant for hematologic malignancies. Consequently, standard therapy for mucositis consists of palliative rinses, such as saline, bicarbonate solutions, mouthwashes, topical analgesics such as lidocaine and/or systemic administration of narcotics.

The complexity of mucositis as a biological process has only been recently appreciated. It has been suggested that the condition represents a sequential interaction of oral mucosal cells and tissues reactive oxygen species, pro-inflammatory cytokines, mediators of apoptosis, a range of signaling pathways, and local factors such as saliva and the oral micro biota. While epithelial degeneration and breakdown ultimately result in mucosal ulceration, it appears that the early changes associated with radiation-induced mucosal toxicity occur within the endothelium, and connective tissue of the submucosa. It appears that the overall mechanism for mucositis development is similar for both radiation and chemotherapy.

1.2 Chemo-Radiation Model of Oral Mucositis with Cis-Platin.

The chemo-radiation model of oral mucositis in hamsters, developed by the Principal Investigator, has proven to be an accurate, efficient and cost-effective technique to provide a preliminary evaluation of anti-mucositis compounds. In this model, hamsters received a single dose of cis-platin at 5 mg/kg on day −1, followed by a single dose of radiation of 35 Gy to the left cheek pouch on day 0, rather than the single dose of 40 Gy on day 0 that is used in acute radiation studies. The course of mucositis in this model is very similar to the acute radiation model and results in peak mucositis scores approximately 16-18 days following radiation.

2. Study Objective and Summary

2.1 Study Objective

The objective of this study was to evaluate the effect of SCV-07, administered by sub-cutaneous injection, on the frequency, severity and duration of oral mucositis induced by a fractionated radiation protocol.

2.2 Study Summary

Hamsters received a single dose of cis-platin at 5 mg/kg on day −1 by intra-peritoneal injection, followed by a single dose of radiation of 35 Gy to the left cheek pouch on day 0. This was accomplished by anesthetizing the animals and everting the left buccal pouch, while protecting the rest of the animal's bodies with a lead shield. Test materials were given by subcutaneous injection once daily as detailed in Table 13. Mucositis was evaluated clinically starting on day 6, and continuing on alternate days until day 28. Test articles were given as from day −1 to day 20.

3. Evaluation

3.1 Mucositis Evaluation

The grade of mucositis was scored, beginning day 6, and for every second day thereafter, through and including day 28. The effect on mucositis of each drug treatment compared to placebo was assessed according to the following parameters:

3.1.1 The Difference in the Number of Days Hamsters in Each Group have Ulcerative (Score ≧3) Mucositis.

On each evaluation day, the number of animals with a blinded mucositis score of ≧3 in each drug treatment group was compared to the control group. Differences were compared on a cumulative basis and statistical significance was determined by chi-square analysis. Efficacy, in this analysis, is defined by a significant reduction in the number of days that a group of animals had ulcerations (scores 3) when compared to the control group.

3.1.2 Rank Sum Differences in Daily Mucositis Scores.

For each evaluation day the scores of the control group were compared to those of the treated groups using non-parametric rank sum analysis. Treatment success was considered as a statistically significant lowering of scores in the treated group on 2 or more days from day 6 to day 28.

3.2 Weights and Survival

All animals were weighed daily and their survival recorded, in order to assess possible differences in animal weight among treatment groups as an indication for mucositis severity and/or possible toxicity resulting from the treatments.

4. Study Design

Forty (40) male Syrian Golden Hamsters were given an intraperitoneal injection of 5 mg/kg Cisplatin on day −1. On day 0 all animals were given an acute radiation dose of 35 Gy directed to their left buccal cheek pouch. This was accomplished by anesthetizing the animals and everting the left buccal pouch, while protecting the rest of the animals with a lead shield. Test materials were given by subcutaneous injection once daily as detailed in Table 13. Mucositis was evaluated clinically starting on Day 6, and continued on alternate days until day 28.

TABLE 13

SCI-04. Study Design

| Group | Number of Animals | Cisplatin | Radiation | Treatment | Treatment Schedule* | Volume (mL) |
|---|---|---|---|---|---|---|
| 1 | 10 males | 5 mg/kg, day −1 | 35 Gy, day 0 | Vehicle (PBS), sc, qd | Day −1 to 20 | Adjust per body weight |
| 2 | 10 males | 5 mg/kg, day −1 | 35 Gy, day 0 | SCV-07, sc, qd 10 µg/kg, | Day −1 to 20 | Adjust per body weight |
| 3 | 10 males | 5 mg/kg, day −1 | 35 Gy, day 0 | SCV-07, sc, qd 100 µg/kg, | Day −1 to 20 | Adjust per body weight |
| 4 | 10 males | 5 mg/kg, day −1 | 35 Gy, day 0 | SCV-07, sc, qd 1.0 mg/kg | Day −1 to 20 | Adjust per body weight |

*The dose on day 0 will be performed 30 minutes prior to radiation

5. Material and Methods

5.1 Location of Study Performance

The study was performed at Biomodels AAALAC-accredited facility in Watertown, Mass. IACUC approval number 07-0620-01 for this study was obtained from Biomodels IACUC.

5.2 Animals

Male LVG Syrian Golden Hamsters (Charles River Laboratories), aged 5 to 6 weeks, with average body weight of 90 g at study commencement, were used. Animals were individually numbered using an ear punch and housed in small groups of approximately 10 animals per cage. Animals were acclimatized for 5 days prior to study commencement and during this period, the animals were observed daily in order to reject animals that present in poor condition.

5.3 Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained.

5.4 Diet

Animals were fed with a Purina Labdiet® 5061 rodent diet and water was provided ad libitum.

5.5 Animal Randomization and Allocations

Animals were randomly and prospectively divided into four (4) treatment groups prior to irradiation. Each animal was identified by an ear punch corresponding to an individual number. For more consistent identification, ear punch numbering was used rather than tagging, since tags may become dislodged during the course of the study. A cage card was used to identify each cage or label marked with the study number (SCI-04), treatment group number and animal numbers.

5.6 Sub-Cutaneous Dosing and Drug Application

The test compound, human SCV-07 peptide was provided as a powder and dissolved in sterile PBS immediately prior to administration. Drug was given in a volume of 0.1, using a tuberculin syringe with a 27 G needle. Injections were given subcutaneously to the back or abdomen.

5.7 Mucositis Induction

In this study, mucositis was induced with a combination of Cis-platin and radiation. Cis-platin was given as a single injection (IP) of 5 mg/kg on day −1. Radiation was given as a single focal dose of 35 Gy on day 0. Radiation was generated with a Philips 160 kVp (kilovolt potential) (18.75-ma) X-ray source at a focal distance of 30 cm, with a 3.0 mm hardened Al filtration system. Irradiation was targeted to the left buccal pouch mucosa at a rate of 3.32 Gy/minute. Calibration of this source with a Victoreen model 530 dosimeter indicated that the dose rate was 28.57 nC/min. Using this calibration, the energy received by each animal at each radiation dose was approximately 688.6 nC (nanoCoulombs). Prior to irradiation, animals were anesthetized with an intraperitoneal injection of ketamine (160 mg/kg) and xylazine (8 mg/kg). The left buccal pouch was everted, fixed and isolated using a lead shield.

5.8 Mucositis Scoring

The mucositis score, weight change and survival were measured throughout the study as described above. For the evaluation of mucositis, the animals were anesthetized with an inhalation anesthetic, and the left pouch everted. Mucositis was scored visually by comparison to a validated photographic scale, ranging from 0 for normal, to 5 for severe ulceration (clinical scoring). In descriptive terms, this scale is defined as follows:

TABLE 14

SCI-04: Mucositis Scoring.

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas, but no frank ulceration. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

6. Results and Discussion

6.1 Survival

No deaths were seen in this study

6.2 Weight Change

There were no significant differences in weight changes between study groups. The mean daily percent weight change data was evaluated. The saline treated control hamsters gained an average of 46.5% of their starting weight during the study. Hamsters in the group receiving SCV-07 at 10 µg/kg on days −1 to 20 gained an average of 51.3% of their starting weight during the study. Hamsters in the group receiving SCV-07 at 100 µg/kg on days −1 to 20 gained an average of 46.7% of their starting weight during the study. Hamsters in the group receiving SCV-07 at 1 mg/kg from day −1 to day 20 gained an average of 48.8% of their starting weight during the study. The significance of these differences was evaluated by calculating the area-under-the-curve (AUC) for the weight gain of each animal, and then comparing the different treatment groups using a One-Way ANOVA test. The results of this analysis indicated that there were no significant differences between the different treatment groups (P=0.663).

6.3 Mucositis (Tables 15 & 16)

The kinetics and severity of mucositis development among control animals was consistent with that which was expected.

Mean daily mucositis scores for each group were evaluated. In the saline treated control group, the mean peak mucositis score was 3.1, which occurred on day 18. The group receiving SCV-07 at 10 µg/kg from day −1 to day 20 had a peak mean mucositis score of 2.9, which occurred on day 16. The group receiving SCV-07 at 100 µg/kg from day −1 to day 20 had a peak mean mucositis score of 2.8, which occurred on days 14 and 16. The group receiving SCV-07 at 1 mg/kg from day −1 to day 20 had a peak mean mucositis score of 3.2, which occurred on day 16. The significance of the differences observed between the different treatment groups was evaluated by calculating the number of days with a score of 3 or higher for each group and comparing these numbers using a chi-squared ($\chi^2$) test. The results of this analysis are shown in Table 15. The hamsters in the saline treated control group had a score of 3 or higher on 50% of the animal days evaluated. In the group receiving SCV-07 at 10 µg/kg from day −1 to day 20, a mucositis score of 3 or higher was observed on 34.2% of the animals days evaluated, which was not statistically significantly different from controls (P<0.001). In the group receiving SCV-07 at 100 µg/kg on days −1 to 20, a mucositis score of 3 or higher was observed on 29.2% of the animals days evaluated, which was statistically significantly different from controls (P<0.001). In the group receiving SCV-07 at 100 µg/kg on days −1 to 20, a mucositis score of 3 or higher was observed on 30.8% of the animals days evaluated, which was not statistically significantly different from controls (P<0.001). A further analysis of the mucositis scores was performed using the Mann-Whitney rank sum analysis to compare the scores for each group on each day. The results of this analysis are shown in Table 16. In this analysis, 2 days of significant reduction in the mucositis score are generally required before it is regarded as meaningful. The group treated with SCV-07 at 10 µg/kg on days −1 to 20, had significantly less mucositis than the saline controls on days 22 (P=0.010), 24 (P=0.022), 26 (P=0.015), and 28 (P<0.001). The group treated with SCV-07 at 100 µg/kg on days −1 to 20, had significantly less mucositis than the saline controls on days 6 (P=0.015), 22 (P=0.003), 24 (P=0.005), 26 (P<0.001), and 28 (P<0.001). The group treated with SCV-07 at 1 mg/kg on days −1 to 20, had significantly less mucositis than the saline controls on days 6 (P=0.015), 20 (P=0.029), 22 (P=0.012), 24 (P=0.001), 26 (P=0.003), and 28 (P<0.001).

TABLE 15

SCI-04. Chi-square analysis of the total number of days the animals in each group spent with a score of three or more. This statistic is a measure of severity of ulceration, a clinically important outcome.

| Group | Days >=3 | Days <3 | Total Days | % Days >=3 | Chi Sq v control | P Value |
|---|---|---|---|---|---|---|
| Vehicle, qd, sc Days −1 to 20 | 120 | 120 | 240 | 50.0 | — | — |
| SCV-07 10 ug/kg, qd, sc Days −1 to 20 | 82 | 158 | 240 | 34.2 | 11.702 | <0.001 |
| SCV-07 100 ug/kg, qd, sc Days −1 to 20 | 70 | 170 | 240 | 29.2 | 20.9160 | <0.001 |
| SCV-07 1 mg/kg, qd, sc Days −1 to 20 | 74 | 166 | 240 | 30.8 | 17.5190 | <0.001 |

TABLE 16

SCI-04. The significance of group differences observed in daily mucositis scores was determined using the Mann-Whitney rank sum test. This nonparametric statistic is appropriate for the visual mucositis scoring scale. The p values for each calculation are shown. Significant reductions in mucositis scores relative to controls are shown underlined.

| Group Comparison | 6 | 8 | 10 | 12 | 14 | 16 | 18 | 20 | 22 | 24 | 26 | 28 |
|---|---|---|---|---|---|---|---|---|---|---|---|---|
| Control vs SCV-7 10 ug/kg, qd, sc Days −1 to 20 | 0.296 | 0.422 | 0.393 | 0.560 | 0.271 | 0.488 | 0.179 | 0.100 | <u>0.010</u> | <u>0.022</u> | <u>0.015</u> | <u><0.001</u> |
| Control vs SCV-7 100 ug/kg, qd, sc Days −1 to 20 | <u>0.015</u> | 0.422 | 0.510 | 0.957 | 0.506 | 0.248 | 0.100 | 0.455 | <u>0.003</u> | <u>0.005</u> | <u><0.001</u> | <u><0.001</u> |
| Control vs SCV-7 1 mg/kg, qd, sc Days −1 to 20 | <u>0.015</u> | 0.282 | 0.146 | 0.924 | 0.506 | 0.634 | 0.112 | <u>0.029</u> | <u>0.012</u> | <u>0.001</u> | <u>0.003</u> | <u><0.001</u> |

7. Conclusions

1. There was no evidence of any toxicity from SCV-07 in this study based on the observations of mortality and weight gain.

2. Animals treated with SCV-07 at 10 µg/kg from day −1 to day 20 showed a statistically significant reduction in the number of days with a mucositis score of 3 or higher (P<0.001), and a significant reduction in mucositis scores on days 22 (P=0.010), 24 (P=0.022), 26 (P=0.015), and 28 (P<0.001).

3. Animals treated with SCV-07 at 100 µg/kg from day −1 to day 20 showed a statistically significant reduction in the number of days with a mucositis score of 3 or higher (P<0.001), and a significant reduction in mucositis scores on days 6 (P=0.015), 22 (P=0.003), 24 (P=0.005), 26 (P<0.001), and 28 (P<0.001).

4. Animals treated with SCV-07 at 1 mg/kg from day −1 to day 20 showed a statistically significant reduction in the number of days with a mucositis score of 3 or higher (P<0.001), and a significant reduction in mucositis scores on days 6 (P=0.015), 20 (P=0.029), 22 (P=0.012), 24 (P=0.001), 26 (P=0.003), and 28 (P<0.001).

9. Appendices

9.1 Appendix 7—Animal Weights

| Group | Animal | \-1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| | | | | | | | | DAY | | | | | | | | | |
| 1 | 1 | 105 | 104 | 100 | 103 | 106 | 108 | 111 | 111 | 113 | 113 | 115 | 116 | 118 | 121 | 119 | 121 |
| 1 | 2 | 88 | 86 | 83 | 89 | 92 | 94 | 96 | 97 | 101 | 103 | 106 | 105 | 104 | 103 | 104 | 108 |
| 1 | 3 | 90 | 92 | 88 | 91 | 95 | 99 | 101 | 103 | 104 | 92 | 105 | 109 | 109 | 108 | 107 | 109 |
| 1 | 4 | 87 | 86 | 83 | 87 | 90 | 93 | 96 | 98 | 100 | 102 | 105 | 106 | 106 | 109 | 109 | 110 |
| 1 | 5 | 106 | 101 | 99 | 105 | 107 | 111 | 113 | 113 | 117 | 118 | 120 | 122 | 120 | 121 | 120 | 124 |
| 1 | 6 | 82 | 83 | 79 | 82 | 84 | 86 | 87 | 89 | 90 | 97 | 96 | 97 | 97 | 98 | 96 | 95 |
| 1 | 7 | 86 | 85 | 84 | 85 | 88 | 90 | 93 | 94 | 95 | 97 | 98 | 99 | 100 | 101 | 103 | 104 |
| 1 | 8 | 82 | 81 | 78 | 83 | 86 | 89 | 92 | 93 | 98 | 105 | 105 | 103 | 103 | 107 | 106 | 107 |
| 1 | 9 | 90 | 89 | 91 | 93 | 95 | 101 | 101 | 103 | 104 | 106 | 107 | 111 | 112 | 113 | 114 | 118 |
| 1 | 10 | 108 | 109 | 104 | 105 | 110 | 112 | 117 | 118 | 120 | 122 | 123 | 126 | 128 | 129 | 124 | 126 |
| 2 | 11 | 77 | 77 | 74 | 78 | 82 | 83 | 86 | 88 | 90 | 92 | 94 | 96 | 98 | 98 | 98 | 99 |
| 2 | 12 | 101 | 102 | 101 | 104 | 111 | 113 | 112 | 114 | 117 | 121 | 122 | 125 | 125 | 128 | 128 | 130 |
| 2 | 13 | 85 | 84 | 83 | 89 | 93 | 95 | 98 | 101 | 103 | 106 | 106 | 112 | 111 | 111 | 112 | 115 |
| 2 | 14 | 82 | 80 | 80 | 86 | 88 | 90 | 93 | 96 | 98 | 101 | 102 | 105 | 105 | 107 | 108 | 109 |
| 2 | 15 | 76 | 77 | 76 | 77 | 79 | 82 | 83 | 84 | 86 | 88 | 91 | 90 | 92 | 91 | 90 | 91 |
| 2 | 16 | 94 | 94 | 91 | 94 | 98 | 101 | 103 | 106 | 108 | 109 | 108 | 109 | 109 | 109 | 108 | 111 |
| 2 | 17 | 74 | 72 | 70 | 77 | 79 | 76 | 81 | 79 | 80 | 83 | 83 | 85 | 87 | 88 | 88 | 90 |
| 2 | 18 | 80 | 78 | 75 | 78 | 81 | 85 | 85 | 89 | 89 | 92 | 92 | 94 | 95 | 94 | 95 | 96 |
| 2 | 19 | 91 | 90 | 87 | 90 | 91 | 93 | 94 | 94 | 97 | 98 | 98 | 100 | 100 | 97 | 98 | 99 |
| 2 | 20 | 92 | 92 | 90 | 95 | 96 | 99 | 100 | 102 | 105 | 106 | 108 | 110 | 111 | 113 | 114 | 114 |
| 3 | 21 | 87 | 84 | 87 | 90 | 94 | 98 | 99 | 98 | 100 | 103 | 106 | 111 | 109 | 111 | 111 | 110 |
| 3 | 22 | 81 | 80 | 75 | 77 | 81 | 84 | 86 | 88 | 87 | 90 | 91 | 95 | 95 | 98 | 96 | 97 |
| 3 | 23 | 85 | 86 | 83 | 86 | 88 | 91 | 93 | 96 | 95 | 98 | 96 | 101 | 100 | 102 | 102 | 103 |
| 3 | 24 | 104 | 102 | 99 | 102 | 106 | 109 | 113 | 112 | 116 | 118 | 118 | 123 | 123 | 126 | 127 | 130 |
| 3 | 25 | 78 | 76 | 73 | 76 | 82 | 83 | 84 | 84 | 87 | 90 | 89 | 95 | 94 | 92 | 92 | 95 |
| 3 | 26 | 92 | 91 | 88 | 90 | 91 | 92 | 95 | 95 | 96 | 98 | 98 | 100 | 101 | 100 | 100 | 100 |
| 3 | 27 | 103 | 103 | 102 | 100 | 108 | 110 | 115 | 118 | 119 | 120 | 120 | 124 | 124 | 127 | 125 | 128 |
| 3 | 28 | 96 | 96 | 91 | 90 | 101 | 114 | 105 | 106 | 107 | 108 | 111 | 113 | 114 | 117 | 116 | 116 |
| 3 | 29 | 83 | 82 | 84 | 87 | 91 | 91 | 94 | 94 | 97 | 98 | 97 | 103 | 101 | 102 | 102 | 101 |
| 3 | 30 | 77 | 78 | 74 | 76 | 78 | 79 | 81 | 83 | 86 | 88 | 88 | 92 | 94 | 93 | 94 | 94 |
| 4 | 31 | 97 | 96 | 94 | 98 | 103 | 106 | 108 | 110 | 111 | 112 | 112 | 113 | 111 | 113 | 113 | 114 |
| 4 | 32 | 96 | 96 | 93 | 95 | 99 | 103 | 104 | 106 | 109 | 110 | 111 | 113 | 113 | 113 | 114 | 113 |
| 4 | 33 | 93 | 91 | 89 | 90 | 94 | 100 | 101 | 103 | 107 | 110 | 110 | 114 | 115 | 114 | 113 | 113 |
| 4 | 34 | 87 | 85 | 85 | 89 | 92 | 96 | 98 | 103 | 104 | 106 | 107 | 109 | 112 | 113 | 113 | 115 |
| 4 | 35 | 100 | 96 | 97 | 101 | 106 | 108 | 111 | 115 | 118 | 105 | 121 | 124 | 122 | 126 | 124 | 124 |
| 4 | 36 | 88 | 88 | 85 | 87 | 93 | 96 | 99 | 103 | 105 | 108 | 109 | 113 | 114 | 118 | 120 | 121 |
| 4 | 37 | 104 | 102 | 104 | 108 | 114 | 115 | 120 | 119 | 123 | 125 | 127 | 128 | 127 | 127 | 122 | 125 |
| 4 | 38 | 97 | 96 | 93 | 93 | 98 | 103 | 105 | 107 | 110 | 113 | 113 | 116 | 116 | 116 | 115 | 114 |
| 4 | 39 | 88 | 88 | 83 | 85 | 93 | 93 | 95 | 95 | 98 | 100 | 102 | 104 | 102 | 104 | 104 | 103 |
| 4 | 40 | 99 | 97 | 99 | 101 | 107 | 107 | 112 | 113 | 115 | 117 | 118 | 120 | 123 | 125 | 125 | 127 |

| Group | Animal | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|
| | | | | | | | DAY | | | | | | | | |
| 1 | 1 | 119 | 121 | 124 | 125 | 126 | 127 | 130 | 133 | 133 | 137 | 137 | 138 | 139 | 140 |
| 1 | 2 | 112 | 110 | 117 | 116 | 120 | 121 | 124 | 125 | 123 | 131 | 134 | 136 | 135 | 139 |
| 1 | 3 | 112 | 117 | 116 | 117 | 118 | 120 | 126 | 127 | 129 | 131 | 132 | 135 | 134 | 138 |
| 1 | 4 | 110 | 109 | 113 | 115 | 115 | 115 | 121 | 120 | 121 | 126 | 126 | 129 | 129 | 133 |
| 1 | 5 | 123 | 125 | 129 | 129 | 129 | 130 | 133 | 136 | 135 | 141 | 141 | 143 | 144 | 144 |
| 1 | 6 | 95 | 96 | 97 | 99 | 99 | 100 | 102 | 107 | 104 | 106 | 107 | 108 | 109 | 111 |
| 1 | 7 | 103 | 104 | 107 | 107 | 108 | 108 | 111 | 113 | 113 | 115 | 118 | 120 | 120 | 122 |
| 1 | 8 | 108 | 109 | 113 | 115 | 115 | 115 | 119 | 122 | 123 | 125 | 127 | 128 | 129 | 132 |
| 1 | 9 | 118 | 117 | 122 | 123 | 123 | 126 | 128 | 130 | 131 | 134 | 135 | 136 | 138 | 138 |
| 1 | 10 | 126 | 128 | 131 | 134 | 134 | 135 | 137 | 139 | 141 | 144 | 147 | 148 | 148 | 151 |
| 2 | 11 | 99 | 100 | 103 | 103 | 105 | 104 | 108 | 110 | 110 | 114 | 115 | 117 | 117 | 119 |
| 2 | 12 | 132 | 132 | 136 | 137 | 138 | 137 | 141 | 144 | 143 | 148 | 150 | 151 | 152 | 156 |
| 2 | 13 | 117 | 119 | 123 | 125 | 125 | 127 | 130 | 133 | 133 | 139 | 139 | 140 | 145 | 146 |
| 2 | 14 | 109 | 109 | 112 | 113 | 113 | 115 | 117 | 120 | 121 | 123 | 124 | 126 | 127 | 130 |
| 2 | 15 | 93 | 92 | 96 | 98 | 100 | 100 | 103 | 104 | 104 | 105 | 108 | 109 | 110 | 113 |
| 2 | 16 | 112 | 112 | 117 | 117 | 118 | 118 | 121 | 122 | 123 | 126 | 126 | 129 | 128 | 132 |
| 2 | 17 | 90 | 90 | 96 | 97 | 99 | 101 | 105 | 104 | 106 | 109 | 113 | 114 | 114 | 117 |
| 2 | 18 | 97 | 96 | 103 | 102 | 101 | 109 | 105 | 108 | 108 | 111 | 112 | 116 | 114 | 116 |
| 2 | 19 | 98 | 99 | 100 | 104 | 103 | 104 | 106 | 107 | 108 | 111 | 113 | 113 | 113 | 115 |
| 2 | 20 | 115 | 117 | 121 | 122 | 123 | 123 | 127 | 131 | 129 | 134 | 136 | 137 | 138 | 143 |
| 3 | 21 | 109 | 110 | 112 | 114 | 115 | 118 | 117 | 123 | 123 | 128 | 127 | 130 | 130 | 133 |
| 3 | 22 | 97 | 98 | 100 | 102 | 103 | 104 | 107 | 109 | 108 | 113 | 112 | 115 | 112 | 117 |
| 3 | 23 | 103 | 103 | 106 | 107 | 110 | 110 | 113 | 114 | 113 | 117 | 117 | 123 | 119 | 123 |
| 3 | 24 | 131 | 132 | 134 | 134 | 140 | 139 | 142 | 146 | 146 | 146 | 148 | 149 | 149 | 154 |
| 3 | 25 | 95 | 97 | 99 | 101 | 101 | 105 | 106 | 108 | 106 | 113 | 115 | 118 | 116 | 120 |

-continued

| | | | | | | | | | | | | | | | |
|---|---|---|---|---|---|---|---|---|---|---|---|---|---|---|---|
| 3 | 26 | 110 | 101 | 103 | 104 | 105 | 106 | 106 | 109 | 109 | 112 | 112 | 113 | 113 | 116 |
| 3 | 27 | 128 | 128 | 129 | 132 | 134 | 136 | 138 | 139 | 138 | 141 | 143 | 146 | 146 | 149 |
| 3 | 28 | 116 | 117 | 119 | 120 | 123 | 123 | 126 | 128 | 128 | 131 | 133 | 132 | 133 | 137 |
| 3 | 29 | 103 | 105 | 106 | 108 | 112 | 112 | 117 | 118 | 117 | 123 | 123 | 125 | 126 | 130 |
| 3 | 30 | 95 | 97 | 100 | 101 | 102 | 102 | 104 | 107 | 107 | 111 | 114 | 116 | 115 | 118 |
| 4 | 31 | 112 | 113 | 114 | 116 | 117 | 120 | 121 | 123 | 124 | 130 | 130 | 133 | 133 | 136 |
| 4 | 32 | 123 | 116 | 118 | 119 | 119 | 122 | 123 | 125 | 124 | 129 | 130 | 132 | 133 | 136 |
| 4 | 33 | 112 | 114 | 117 | 119 | 122 | 122 | 126 | 129 | 128 | 133 | 137 | 138 | 138 | 141 |
| 4 | 34 | 116 | 116 | 120 | 120 | 123 | 122 | 125 | 126 | 127 | 129 | 131 | 131 | 131 | 133 |
| 4 | 35 | 114 | 123 | 127 | 130 | 130 | 132 | 137 | 141 | 139 | 142 | 147 | 147 | 145 | 150 |
| 4 | 36 | 118 | 119 | 120 | 123 | 123 | 125 | 128 | 130 | 129 | 134 | 136 | 139 | 137 | 142 |
| 4 | 37 | 125 | 128 | 131 | 132 | 134 | 135 | 139 | 143 | 143 | 145 | 148 | 150 | 150 | 153 |
| 4 | 38 | 115 | 115 | 119 | 119 | 121 | 122 | 123 | 125 | 126 | 128 | 130 | 133 | 132 | 135 |
| 4 | 39 | 105 | 107 | 110 | 112 | 114 | 114 | 115 | 117 | 116 | 119 | 123 | 126 | 125 | 130 |
| 4 | 40 | 125 | 128 | 131 | 134 | 135 | 133 | 138 | 142 | 144 | 148 | 149 | 152 | 151 | 155 |

9.2 Appendix 8—Mucositis Scores

| Group | Animal | \multicolumn{12}{c}{DAY} |
|---|---|---|---|---|---|---|---|---|---|---|---|---|---|

| Group | Animal | 6 | 8 | 10 | 12 | 14 | 16 | 18 | 20 | 22 | 24 | 26 | 28 |
|---|---|---|---|---|---|---|---|---|---|---|---|---|---|
| 1 | 1 | 2 | 0 | 1 | 2 | 3 | 3 | 3 | 3 | 3 | 3 | 3 | 3 |
| 1 | 1 | 1 | 0 | 1 | 2 | 3 | 3 | 3 | 3 | 3 | 3 | 3 | 3 |
| 1 | 2 | 1 | 1 | 2 | 3 | 3 | 3 | 3 | 3 | 3 | 2 | 2 | 2 |
| 1 | 2 | 0 | 0 | 2 | 3 | 3 | 3 | 4 | 3 | 3 | 2 | 2 | 2 |
| 1 | 3 | 2 | 1 | 2 | 3 | 4 | 4 | 3 | 3 | 3 | 3 | 3 | 3 |
| 1 | 3 | 1 | 1 | 2 | 3 | 3 | 4 | 3 | 3 | 3 | 3 | 3 | 3 |
| 1 | 4 | 0 | 0 | 1 | 2 | 2 | 3 | 3 | 3 | 3 | 3 | 3 | 3 |
| 1 | 4 | 0 | 0 | 1 | 2 | 2 | 3 | 3 | 3 | 3 | 3 | 3 | 3 |
| 1 | 5 | 2 | 1 | 2 | 3 | 3 | 3 | 3 | 3 | 3 | 3 | 3 | 3 |
| 1 | 5 | 1 | 1 | 2 | 2 | 3 | 3 | 3 | 3 | 3 | 3 | 3 | 3 |
| 1 | 6 | 1 | 0 | 1 | 2 | 3 | 3 | 3 | 3 | 3 | 2 | 2 | 2 |
| 1 | 6 | 0 | 0 | 1 | 2 | 3 | 3 | 3 | 3 | 3 | 2 | 2 | 2 |
| 1 | 7 | 0 | 0 | 1 | 1 | 2 | 2 | 2 | 2 | 2 | 2 | 1 | 1 |
| 1 | 7 | 0 | 0 | 0 | 1 | 2 | 2 | 2 | 2 | 2 | 2 | 1 | 1 |
| 1 | 8 | 1 | 0 | 1 | 2 | 3 | 3 | 3 | 3 | 3 | 2 | 2 | 2 |
| 1 | 8 | 0 | 0 | 1 | 2 | 3 | 3 | 4 | 3 | 3 | 2 | 2 | 2 |
| 1 | 9 | 0 | 0 | 1 | 3 | 3 | 3 | 3 | 3 | 3 | 2 | 2 | 1 |
| 1 | 9 | 0 | 0 | 1 | 3 | 3 | 3 | 3 | 3 | 3 | 2 | 2 | 1 |
| 1 | 10 | 0 | 0 | 1 | 2 | 4 | 3 | 4 | 3 | 3 | 3 | 2 | 2 |
| 1 | 10 | 0 | 0 | 0 | 2 | 4 | 4 | 4 | 3 | 3 | 3 | 2 | 2 |
| 2 | 11 | 0 | 0 | 1 | 2 | 2 | 3 | 2 | 3 | 2 | 2 | 1 | 0 |
| 2 | 11 | 0 | 0 | 1 | 2 | 2 | 3 | 2 | 3 | 2 | 1 | 1 | 0 |
| 2 | 12 | 1 | 0 | 2 | 2 | 2 | 2 | 2 | 2 | 1 | 1 | 1 | 0 |
| 2 | 12 | 0 | 0 | 1 | 2 | 2 | 2 | 2 | 2 | 1 | 1 | 1 | 0 |
| 2 | 13 | 1 | 0 | 1 | 3 | 3 | 3 | 3 | 2 | 2 | 2 | 1 | 0 |
| 2 | 13 | 0 | 0 | 1 | 3 | 3 | 3 | 3 | 1 | 2 | 2 | 1 | 0 |
| 2 | 14 | 1 | 0 | 1 | 2 | 2 | 3 | 3 | 3 | 3 | 3 | 3 | 2 |
| 2 | 14 | 0 | 0 | 1 | 2 | 3 | 3 | 3 | 3 | 3 | 3 | 3 | 2 |
| 2 | 15 | 1 | 0 | 1 | 2 | 3 | 3 | 3 | 3 | 3 | 2 | 2 | 1 |
| 2 | 15 | 0 | 0 | 1 | 2 | 3 | 3 | 3 | 3 | 3 | 2 | 1 | 1 |
| 2 | 16 | 1 | 1 | 2 | 3 | 3 | 2 | 2 | 2 | 1 | 1 | 1 | 0 |
| 2 | 16 | 0 | 0 | 2 | 3 | 3 | 2 | 2 | 2 | 1 | 1 | 1 | 1 |
| 2 | 17 | 1 | 0 | 2 | 3 | 3 | 4 | 3 | 3 | 2 | 2 | 2 | 1 |
| 2 | 17 | 0 | 0 | 2 | 3 | 3 | 4 | 3 | 3 | 2 | 2 | 2 | 1 |
| 2 | 18 | 0 | 0 | 2 | 2 | 3 | 3 | 3 | 2 | 2 | 3 | 1 | 1 |
| 2 | 18 | 0 | 0 | 1 | 2 | 3 | 3 | 3 | 2 | 2 | 3 | 1 | 1 |
| 2 | 19 | 0 | 0 | 1 | 3 | 3 | 3 | 4 | 3 | 3 | 2 | 3 | 3 |
| 2 | 19 | 0 | 0 | 1 | 3 | 3 | 3 | 4 | 3 | 3 | 2 | 3 | 3 |
| 2 | 20 | 0 | 1 | 2 | 2 | 3 | 3 | 3 | 3 | 2 | 2 | 2 | 2 |
| 2 | 20 | 0 | 0 | 2 | 2 | 3 | 3 | 3 | 3 | 2 | 2 | 2 | 1 |

The invention claimed is:

1. A method for reducing the amount of mucosal deterioration, injury, or damage to at least one of oral and esophageal mucosal tissues, the mucosal deterioration, injury, or damage resulting from radiation treatment in a subject undergoing radiation therapy for head and neck cancer, the method comprising: administering to said subject an effective amount of γ-D-glutamyl-L-tryptophan or a pharmaceutically acceptable salt thereof.

2. The method of claim 1, wherein the oral and/or esophageal mucosal deterioration, injury, or damage comprises ulcerative lesions.

3. The method of claim 1, wherein said radiation is administered at a cumulative dose of at least about 15 Gy.

4. The method of claim 1, wherein said radiation is administered at a cumulative dose of at least about 40 Gy.

5. The method of claim 1, wherein said radiation is administered at a cumulative dose of at least about 60 Gy.

6. The method of claim 1, wherein a chemotherapy is administered to the subject.

7. The method of claim 6, wherein the chemotherapy is cis-platin.

8. The method of claim 7, wherein said cis-platin is administered at a dosage within a range of 0.1-50 mg/kg.

9. The method of claim 7, wherein said cis-platin is administered at a dosage of about 5 mg/kg.

10. The method of claim 1 wherein said γ-D-glutamyl-L-tryptophan or a pharmaceutically acceptable salt thereof is administered before radiation exposure.

11. The method of claim 1 wherein said γ-D-glutamyl-L-tryptophan or a pharmaceutically acceptable salt thereof is administered during radiation exposure.

12. The method of claim 1 wherein said γ-D-glutamyl-L-tryptophan or a pharmaceutically acceptable salt thereof is administered after radiation exposure.

13. The method of claim 1 wherein said γ-D-glutamyl-L-tryptophan or a pharmaceutically acceptable salt thereof is administered before administration of 7-8 Gy of radiation.

* * * * *